United States Patent
Siripragada et al.

(12) 
(10) Patent No.: US 10,414,766 B2
(45) Date of Patent: Sep. 17, 2019

(54) POLYMORPH OF RIOCIGUAT AND ITS PROCESS FOR THE PREPARATION

(71) Applicant: ALEMBIC PHARMACEUTICALS LIMITED, Vadodara (IN)

(72) Inventors: Mahender Rao Siripragada, Vadodara (IN); Mahendar Velisoju, Vadodara (IN); Tejas Shah, Vadodara (IN); Chetan Patil, Vadodara (IN); Kalpesh Jadav, Vadodara (IN); Ashvinkumar Bhuva, Vadodara (IN); Saisuryanaraya Donthukurthi, Vadodara (IN)

(73) Assignee: ALEMBIC PHARMACEUTICALS LIMITED, Gujarat (IN)

( * ) Notice: Subject to any disclaimer, the term of this patent is extended or adjusted under 35 U.S.C. 154(b) by 0 days.

(21) Appl. No.: 16/063,196

(22) PCT Filed: Dec. 12, 2016

(86) PCT No.: PCT/IB2016/057531
§ 371 (c)(1),
(2) Date: Jun. 15, 2018

(87) PCT Pub. No.: WO2017/103760
PCT Pub. Date: Jun. 22, 2017

(65) Prior Publication Data
US 2019/0002461 A1    Jan. 3, 2019

(51) Int. Cl.
*C07D 471/04*    (2006.01)

(52) U.S. Cl.
CPC ........ *C07D 471/04* (2013.01); *C07B 2200/13* (2013.01)

(58) Field of Classification Search
CPC ............................ C07D 471/04; C07D 403/04
USPC ......................................................... 544/328
See application file for complete search history.

(56) References Cited

U.S. PATENT DOCUMENTS

| | | | | |
|---|---|---|---|---|
| 2006/0052397 | A1* | 3/2006 | Alonso-Alija | A61K 31/506 514/256 |
| 2007/0032481 | A1* | 2/2007 | Dvorak | A61K 31/343 514/227.8 |
| 2007/0173509 | A1* | 7/2007 | Buzard | C07D 233/64 514/252.19 |
| 2013/0310563 | A1* | 11/2013 | Mais | C07D 471/04 544/328 |

OTHER PUBLICATIONS

Serajuddin, Advanced Drug Delivery Reviews 59 (2007) 603-616.*
Bastin et al., Organic Process Research & Development 2000, 4, 427-435.*
Liu, Rong, ed., Water-Insoluble Drug Formulation (CRC Press, 2008) Chapter 15 pp. 417-435.*
Morris, et al., International Journal of Pharmaceutics 105 (1994) 209-217.*
Adeyeye, Moji, ed., Preformulation in Solid Dosage Form Development (Informa Healthcare, 2008) Chapter 2.3, pp. 63-80.*
Swarbrick et al., eds. Encyclopedia of Pharmaceutical Technology 13 (Marcel Dekker, NY 1996) pp. 453-499.*
Gould, International J. of Therapeutics 33, 201-213 (1986).*

* cited by examiner

*Primary Examiner* — Deepak R Rao
(74) *Attorney, Agent, or Firm* — Benesch, Friedlander, Coplan & Aronoff LLP

(57) ABSTRACT

The present invention relates to novel polymorph of riociguat and process for preparing the polymorph. The present invention also relates to the improved process for the preparation of riociguat.

12 Claims, 6 Drawing Sheets

POLYMORPH OF RIOCIGUAT AND ITS PROCESS FOR THE PREPARATION

RELATED APPLICATIONS

This application is a national stage entry under 35 USC § 371 of PCT/IB2016/05753, filed 12 Dec. 2016. This application claims the benefit of priority of Indian Pat. App. Nos. 4697/MUM/2015, filed on 15 Dec. 2015, 201621014893, filed on 28 Apr. 2016, and 201621034373 filed on 7 Oct. 2016. The entire contents of each of the preceding documents is incorporated herein by reference.

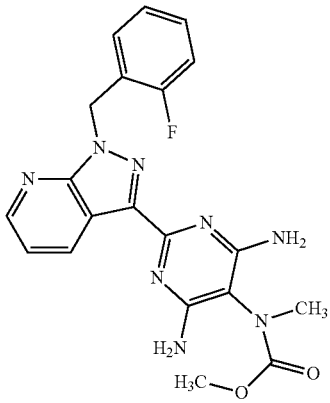

Formula I

FIELD OF THE INVENTION

The present invention relates to a novel polymorph AL of Riociguat and a process for its preparation. The present invention also relates to an improved process for the preparation of riociguat.

BACKGROUND OF THE INVENTION

Riociguat is chemically described as Methyl N-[4,6-Diamino-2-[1-[(2-fluorophenyl)methyl]-1H-pyrazolo[3,4-b]pyridin-3-yl]-5-pyrimidinyl]-N-methyl-carbamate represented by structural Formula I.

Riociguat is the first of a new class of Guanylatecyclase (sGC) agonists, which directly activates sGC and increases low levels of NO sensitivity, for treating pulmonary hypertension and chronic obstructive pulmonary hypertension.

U.S. Pat. No. 7,173,037 discloses a preparation method of the compound of Formula I wherein the compound of Formula I is obtained by recrystallization from methanol.

US20110130410 disclose a DMSO solvate of the compound of Formula I.

WO2015055124 A1 discloses crystalline form I, form II, form III, form IV, and an amorphous form of the compound of Formula I.

WO2003095451A1 discloses a preparation method of the compound of Formula I as shown below in scheme I.

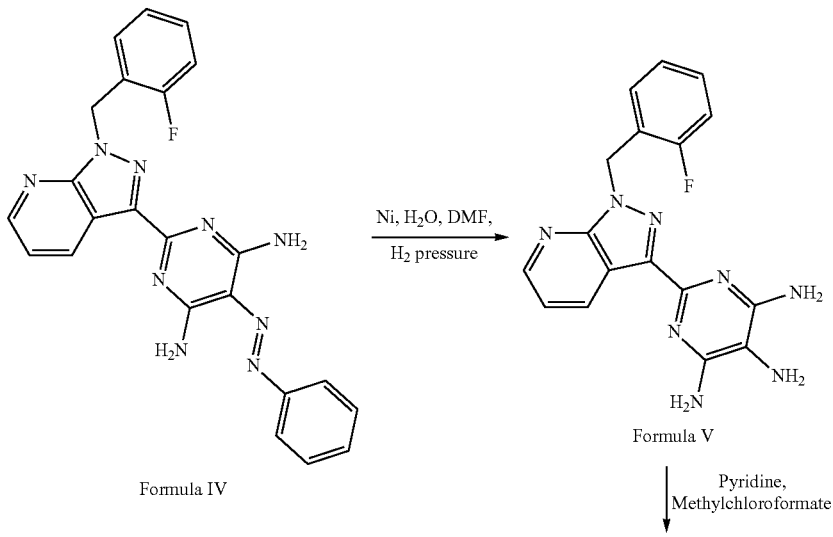

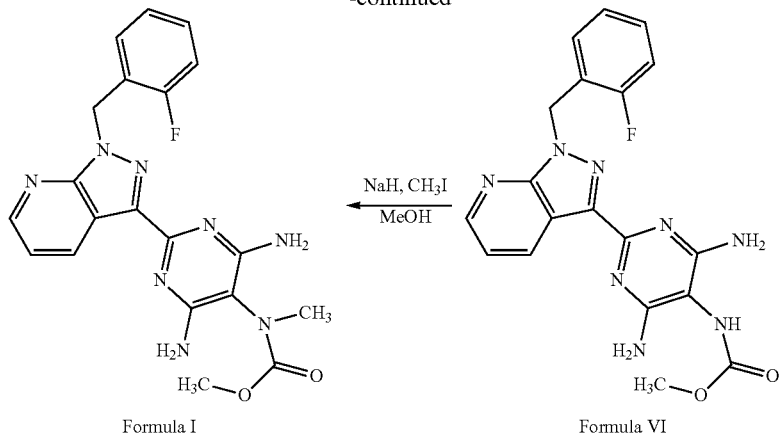
Formula I    Formula VI
WO2011064171A2 also discloses a preparation method of the compound of Formula I as shown below in scheme 2.
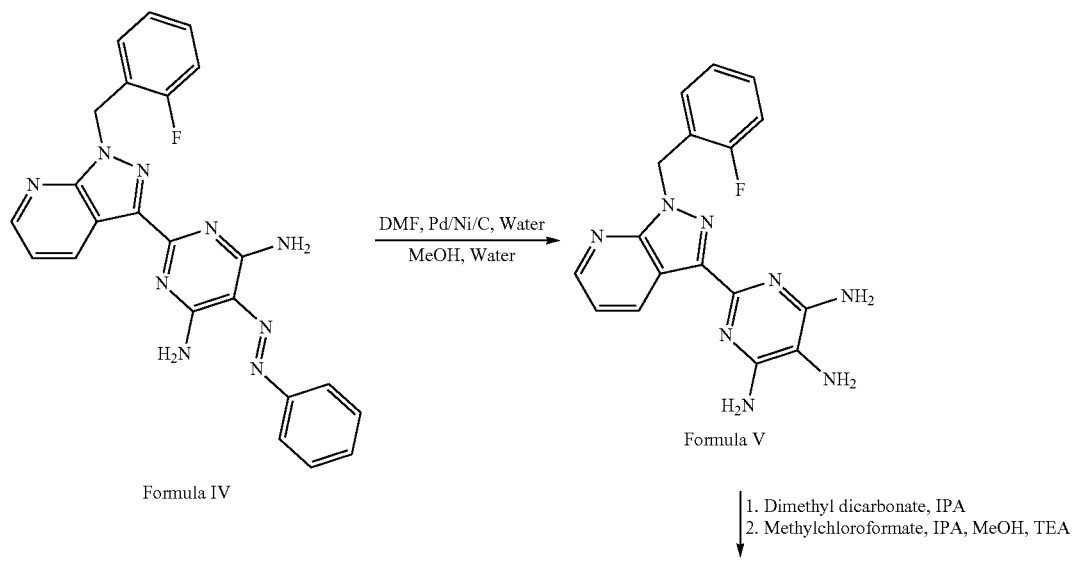
Formula IV    Formula V
1. Dimethyl dicarbonate, IPA
2. Methylchloroformate, IPA, MeOH, TEA
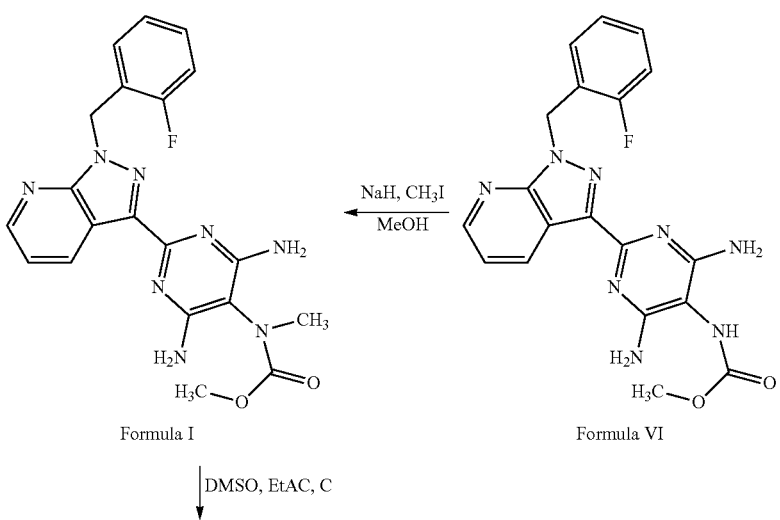
Formula I    Formula VI
DMSO, EtAC, C

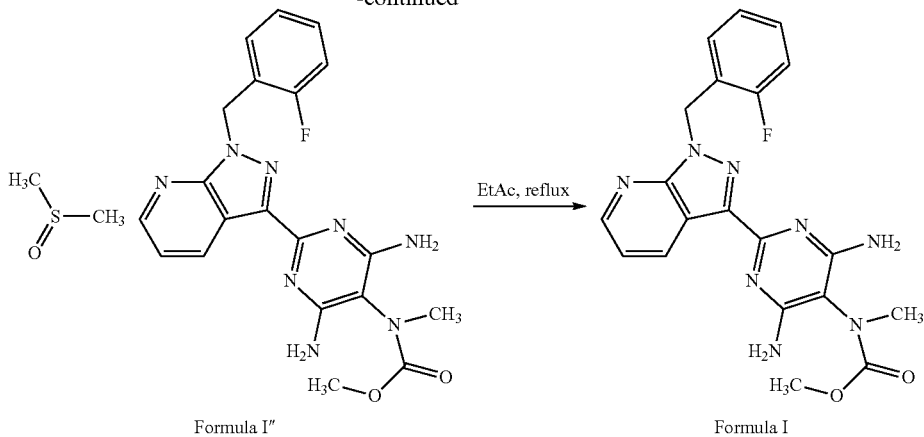

Formula I″ → (EtAc, reflux) → Formula I

Synthesis and purification as reported in WO2003095451A1 have a number of disadvantages which are very unfavorable for industrial realization on a large scale. This is true especially for the isolation of the trisamino compound as trihydrochloride of the compound of formula (IV). The addition of hydrochloric acid requires an acid-proof industrial plant, and the yield of the step is only an unsatisfactory 59.3% of theory (see, for example, Example 8A of WO 03/095451). The realization of the reaction of the trisamino compound of formula (IV) or the corresponding HCl-free base in the solvent pyridine is likewise disadvantageous. The compound of formula (VI) can only be isolated by complete evaporation of the reaction mixture, which is disadvantageous on an industrial scale (see, for example, Example 5 of WO 03/095451). On a relatively large scale, such steps generally result in considerable problems such as sticking-on or thermal decomposition owing to the substantially longer thermal stress when a reaction is carried out on a relatively large scale. The purification of the product represented by formula (VI) according to the experimental procedure of Example 5 from WO 03/095451 by boiling in diethyl ether also has considerable disadvantages. Because of the high flammability of diethyl ether, this step can be realized only with increased industrial expenditure.

However, particularly disadvantageous are the purification processes for the crude product of the formula (I). An effective purification is a condition sine qua non for use as a pharmaceutically active compound. The described purification via RP HPLC, i.e. the chromatographic purification, is a laboratory method, the realization of which on an industrial scale is very expensive. In addition, the stated yield of only 29% for the synthesis step to the crude product of the formula (I) and its purification is very low. The alternative preparation and purification method is very complicated. It comprises a total of 5 isolations of solids (2 concentrations to dryness and 3 filtrations), and, as already mentioned above, concentrations to dryness on an industrial scale are very unfavorable. Altogether, when carrying out a chemical step, a number of 5 isolations of solids for the preparation and purification of a pharmaceutically active compound on an industrial scale is very disadvantageous.

It has been the endeavor of pharmaceutical scientists to provide novel and stable forms of drug substances, which would have the strengths of thermodynamic stability, enhanced solubility, rapid onset of action and an enhanced bioavailability. However, it is well known in the art that polymorphism is unpredictable, both as regards the uncertainty that any new forms will be found, and the lack of any standard methods for preparing a new form. This has been discussed in the literature, such as A. Goho, "Tricky Business," Science News, Vol. 166(8), Aug. 21, 2004, and A. M. Rouhi, "The Right Stuff," Chemical and Engineering News, Feb. 24, 2003, pages 32-35.

Therefore, it would be desirable to provide stable polymorph of Riociguat and processes for their preparation, which are commercially viable. Another object to provide a simplified process which is safe and can also be carried out advantageously on an industrial scale and which supports an active compound in high yield and high purity in pharmaceutically acceptable quality.

OBJECT OF THE INVENTION

It is an object of the present invention to provide a novel crystalline form AL of Riociguat of Formula I.

It is an object of the present invention to provide an improved process for the preparation of the novel crystalline form AL of Riociguat of Formula I that is operationally simple and easy to handle at commercial scale.

It is an object of the present invention to provide new acid addition salts of Riociguat including their hydrates, solvates, anhydrous form, and non-solvated form in crystalline and amorphous forms.

It is an object of the present invention to provide an improved process for the preparation of Riociguat of Formula I that is operationally simple and easy to handle at commercial scale.

SUMMARY OF THE INVENTION

In one aspect, the present invention encompasses a process for the preparation of Riociguat of Formula I.

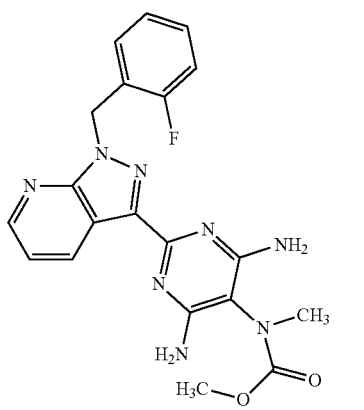

Formula I

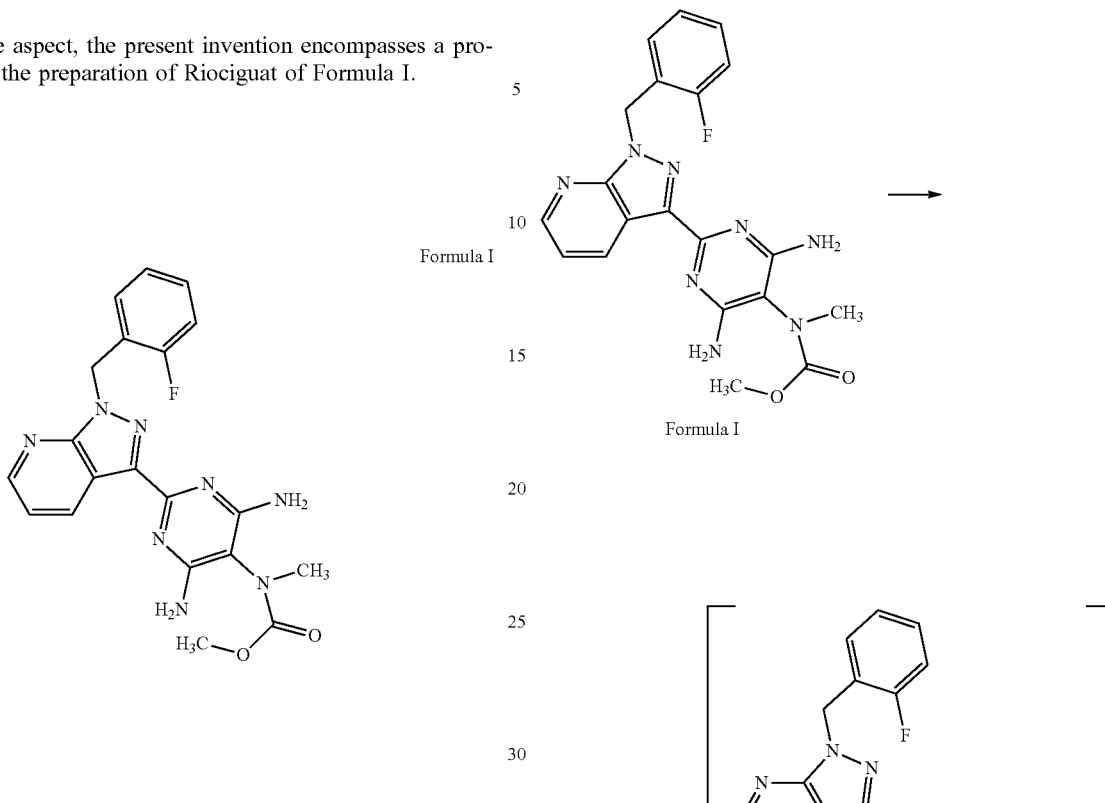

Formula I

In another aspect, the present invention encompasses a process for the preparation of Riociguat of formula I, comprising the steps of:

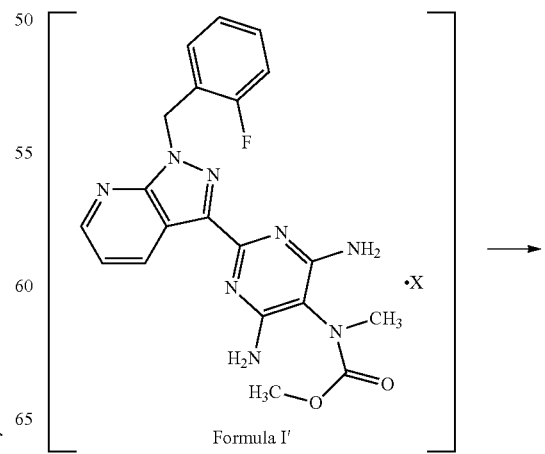

Formula I a) reaction of a compound of formula I with a suitable acid in a suitable solvent to give a compound of formula I' which optionally was isolated, b) reaction of a compound of formula I' with a suitable base in a suitable solvent to give the compound of formula I.

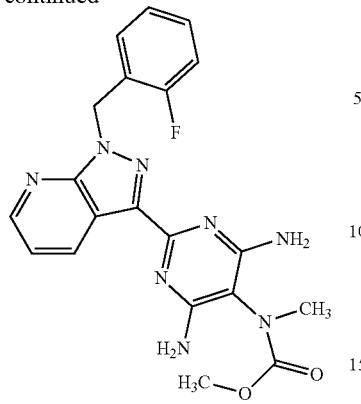

Formula I

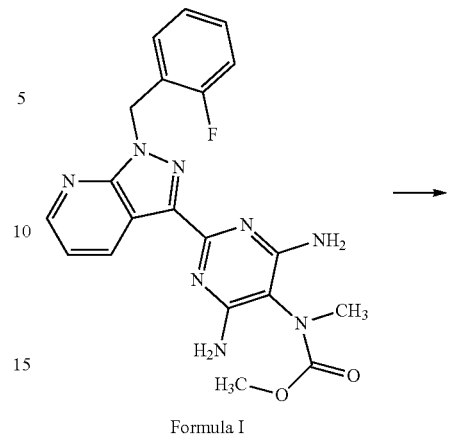

Formula I

In another aspect, the present invention encompasses a process for the preparation of Riociguat of formula I comprising the steps of:

a) reacting a compound of formula I with a suitable acid in a suitable solvent to give acid addition salts of the compound of formula I, b) reacting the acid addition salts of the compound of formula I with a suitable base in a suitable solvent to give the compound of Formula I.

In another aspect of the present invention encompasses a crystalline form AL of riociguat.

In another aspect, the present invention encompasses a process for the preparation of a form AL of Riociguat of Formula I comprising the steps of:

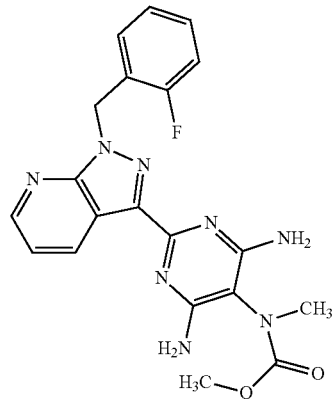

Formula I a) reaction of a compound of Formula I with a suitable acid in a suitable solvent to give a compound of Formula I″ which optionally was isolated,

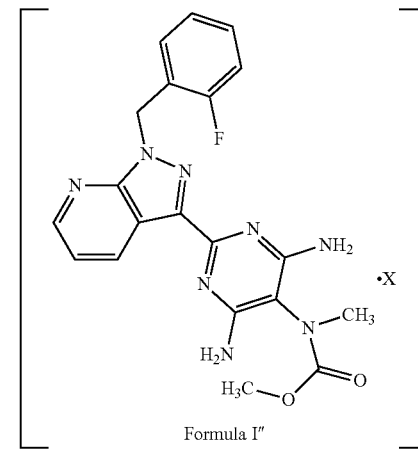

Formula I″ b) reaction of the compound of Formula I″ with a suitable base in a suitable solvent to give the compound of Formula I.

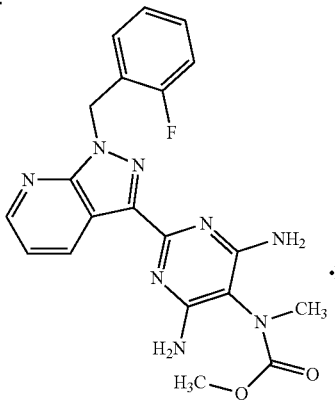

Formula I″

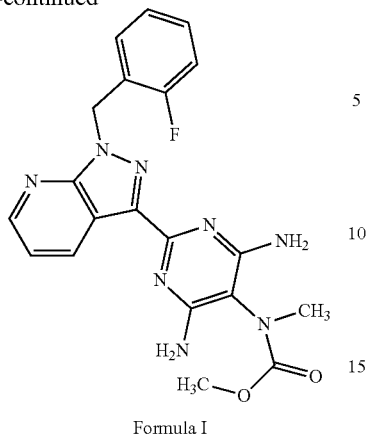

Formula I

In another aspect, the present invention encompasses the acid addition salts of Riociguat including their hydrates, solvates, anhydrous form and non solvated form, in crystalline and amorphous forms.

In another aspect, the present invention encompasses a process for the preparation of acid addition salts of Riociguat comprising reacting Riociguat of Formula I with a suitable acid in the presence of solvent.

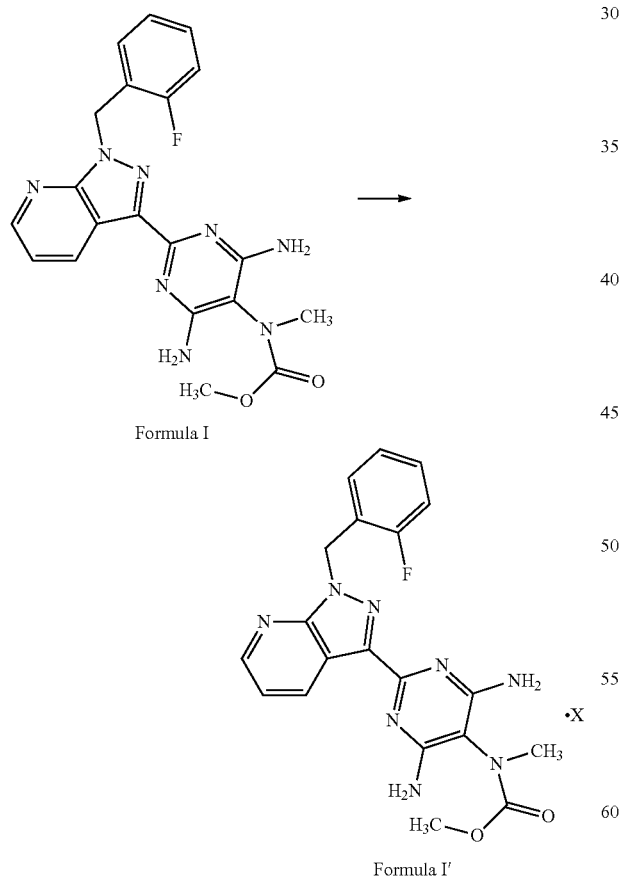

In another aspect, the present invention encompasses use of acid addition salts of Riociguat for the preparation of the crystalline form AL of riociguat.

In another aspect, the present invention encompasses a process for the preparation of Riociguat comprising reacting an acid addition salt of Riociguat with a suitable base in the presence of a suitable solvent.

In another aspect, the present invention encompasses a process for the preparation of the crystalline form AL of Riociguat of Formula I comprising the steps of:

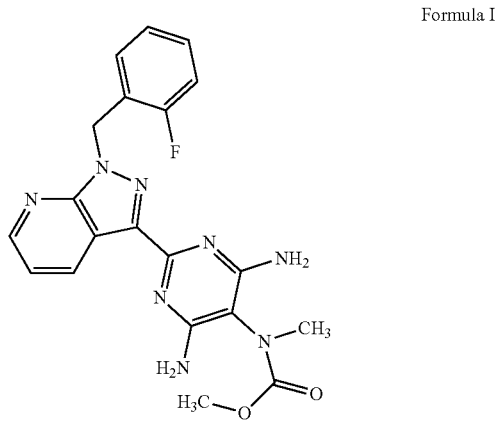 [SMILES: COC(=O)N(C)c1c(N)nc(-c2nn(Cc3ccccc3F)c3ncccc23)nc1N]

Formula I a) reaction of a compound of Formula II with a compound of Formula III in the presence of a suitable base in a suitable solvent to obtain a compound of Formula IV which optionally was isolated,

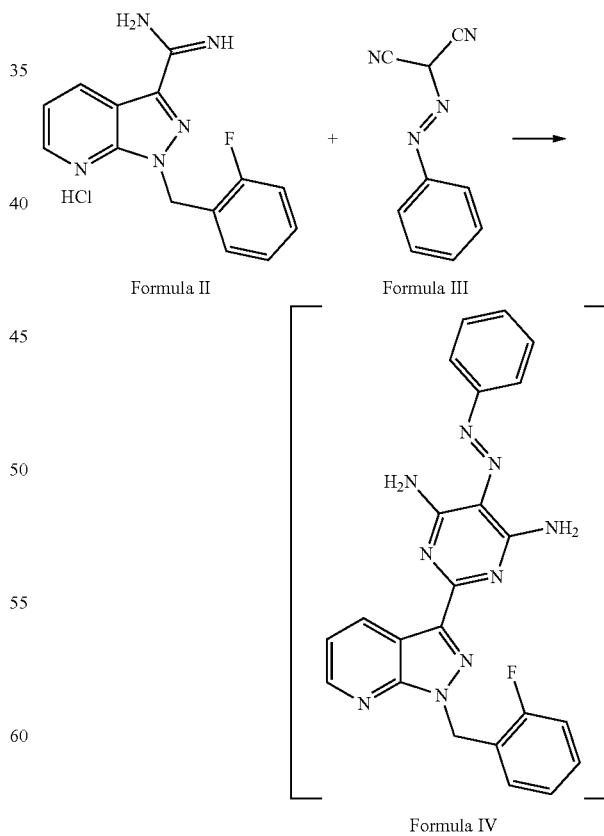

b) catalytic hydrogenation of the compound of Formula IV with a suitable catalyst in a suitable solvent in the presence of hydrogen to give a compound of Formula V, in situ reacting the compound of Formula V in the presence of methyl chloroformate and a suitable base to obtain a compound of Formula VI,

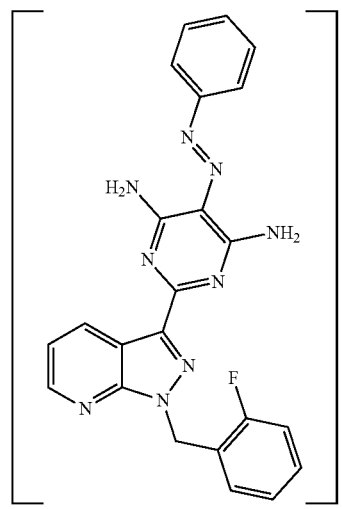

Formula IV

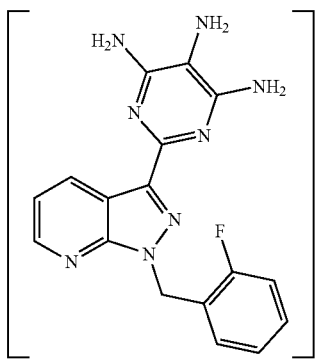

Formula V

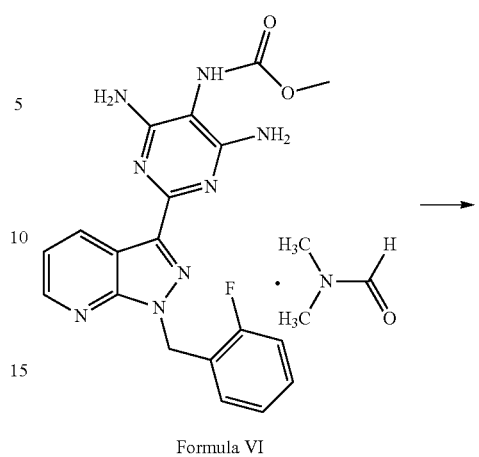

Formula VI

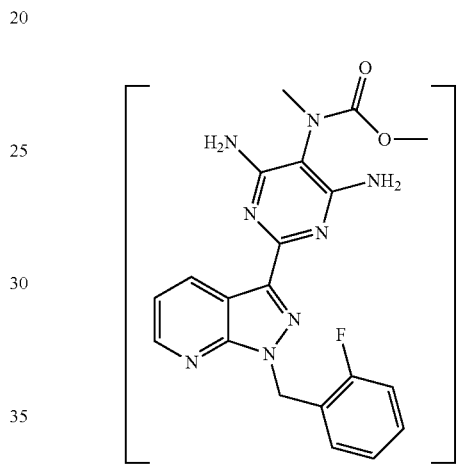

Formula I

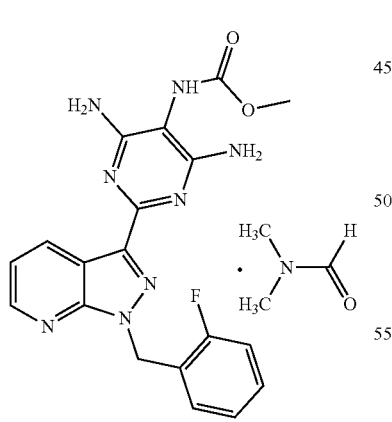

Formula VI

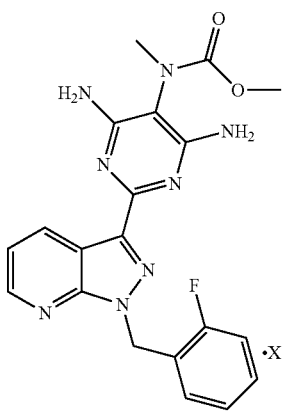

Formula I' c) N-methylation of the compound of Formula VI with a methylating agent in the presence of a suitable base in a suitable solvent to obtain crude Riociguat of Formula I which optionally was isolated and further treated with a suitable acid in a suitable solvent to obtain the compound of Formula I', d) treating the compound of Formula I' with a suitable base in a suitable solvent to obtain the compound of formula I which optionally was isolated and further treated with a suitable acid in a suitable solvent to obtain the compound of Formula I" which optionally was isolated,

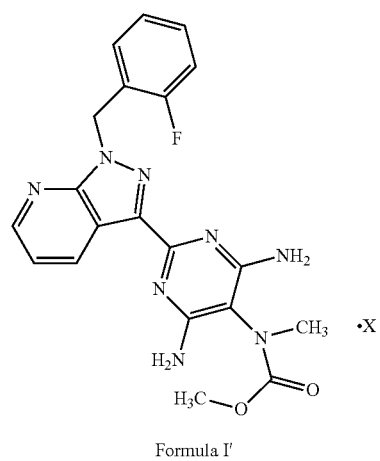

Formula I'

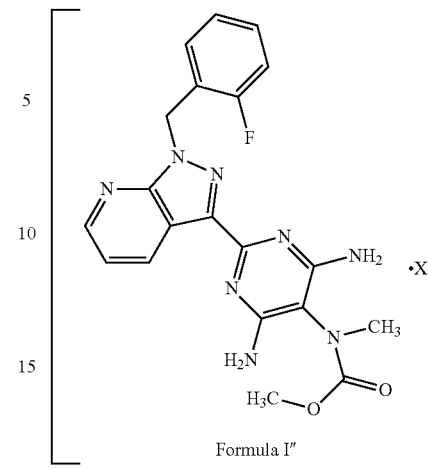

Formula I"

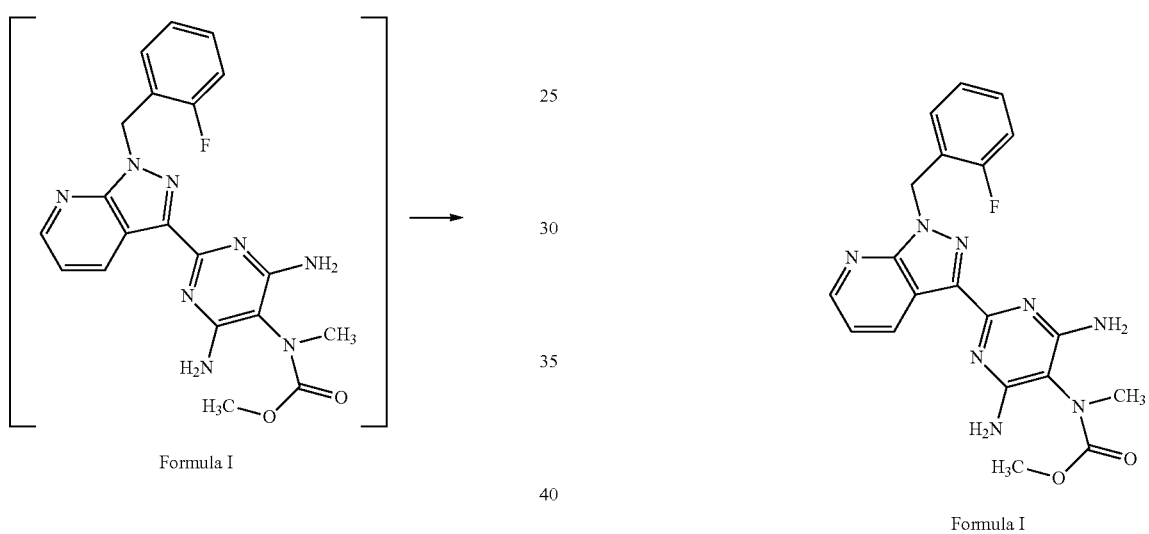

Formula I

Formula I"

Formula I e) treating the compound of Formula I" with a suitable base in a suitable solvent to obtain the crystalline form AL of Riociguat of Formula I.

DETAILED DESCRIPTION OF THE INVENTION

Figure 1:
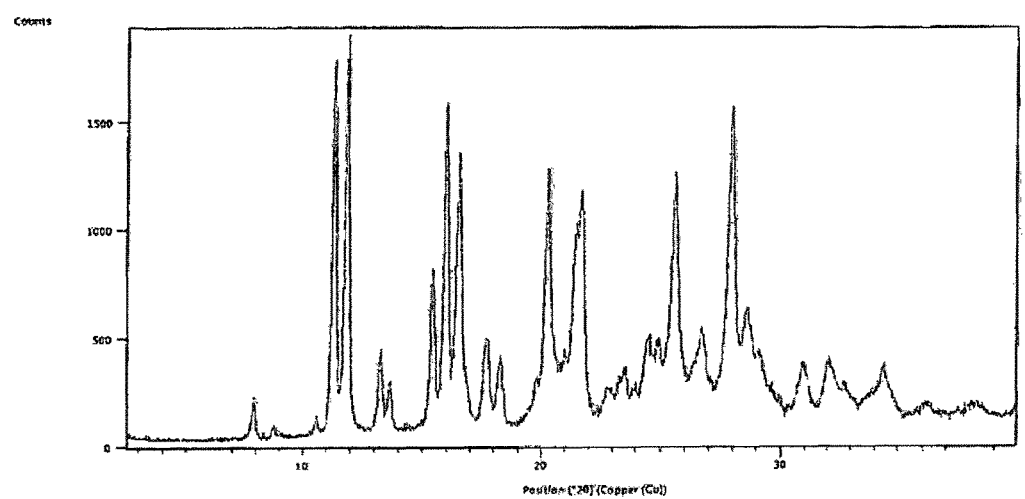
FIG. 1: shows the X-ray powder diffraction pattern of form AL of riociguat.

Riociguat used for the process of the present invention can be prepared by any process known in the art or any method known per se and includes crystalline, amorphous hydrates and solvated forms thereof.

In one embodiment, the present invention encompasses a process for the preparation of form AL of Riociguat of Formula I.

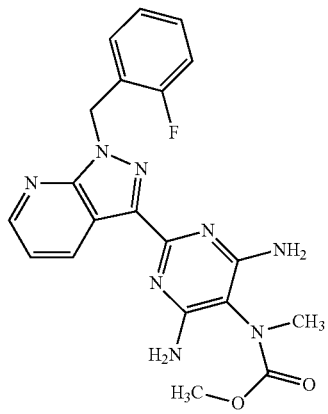

Formula I

In another embodiment, the present invention encompasses a process for the preparation of form AL of Riociguat of Formula I which comprises the steps of:

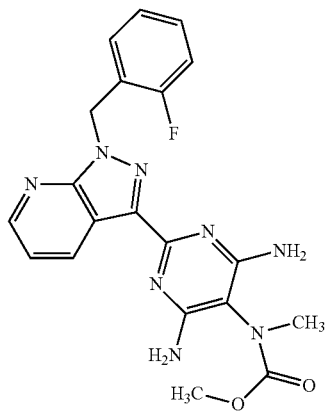

Formula I a) reaction of a compound of formula I with a suitable acid in a suitable solvent to give a compound of Formula I″ which optionally was isolated,

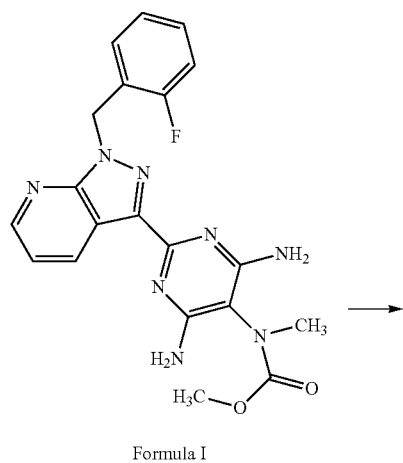

Formula I

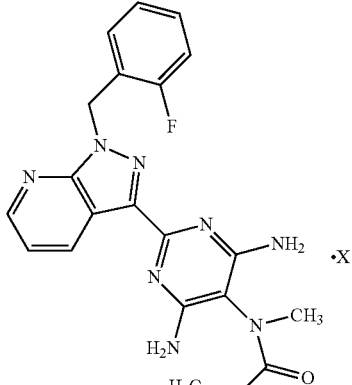

Formula I″ b) reaction of the compound of Formula I″ with a suitable base in a suitable solvent to give the compound of Formula I.

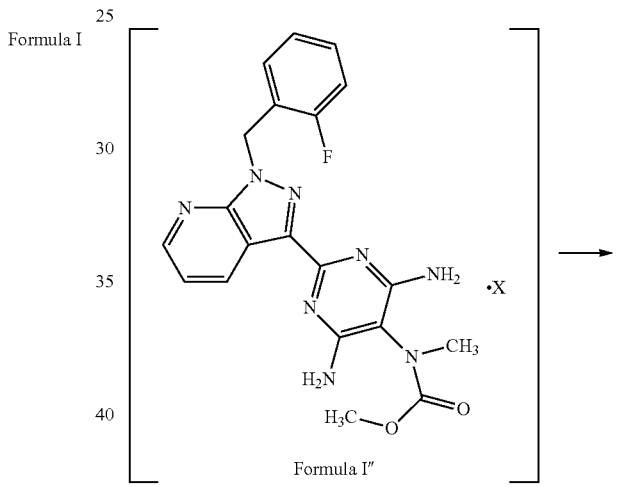

Formula I″

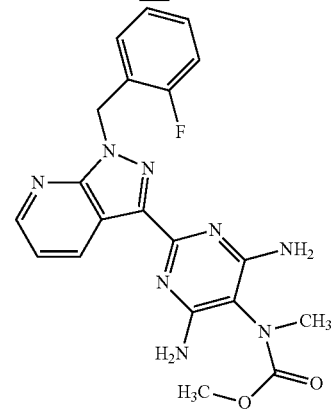

Formula I

In another embodiment, the present invention encompasses the process for the preparation of Riociguat of formula I comprising the steps of:

c) reacting the compound of formula I with a suitable acid in a suitable solvent to give acid addition salts of the compound of formula I, d) reacting the acid addition salts of the compound of formula I with a suitable base in a suitable solvent to give the compound of Formula I.

In another embodiment, the present invention encompasses a process for the preparation of form AL of Riociguat of Formula I which comprises the steps of:

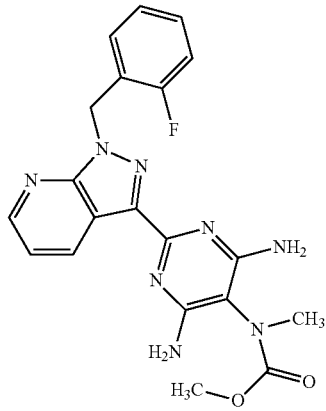

Formula I a) reaction of a compound of formula I with oxalic acid acid and methanol to give a compound of Formula I″ which optionally was isolated,

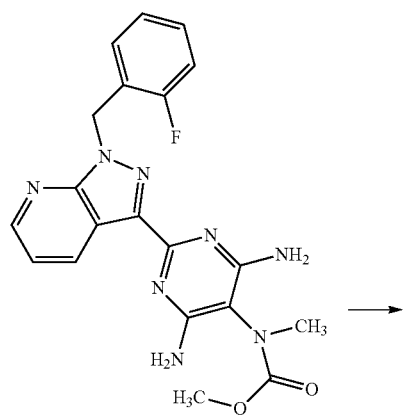

Formula I

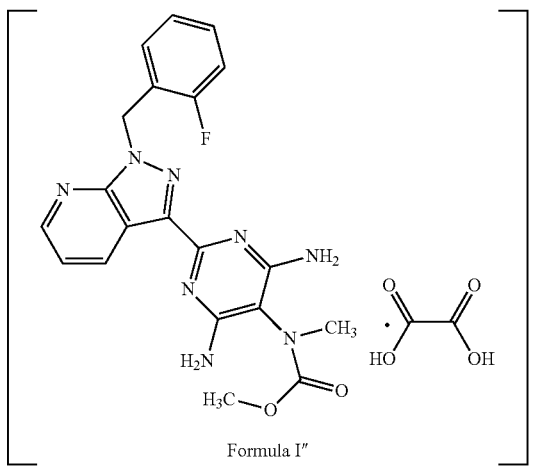

Formula I″ b) reaction of a compound of Formula I″ with sodium hydroxide and water to give form AL of Riociguat of Formula I.

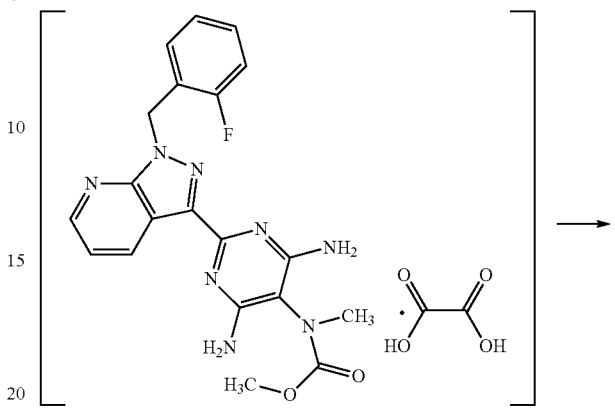

Formula I″

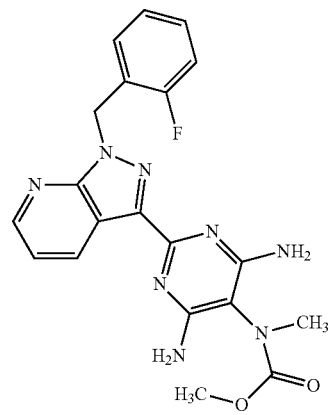

Formula I

In another embodiment, the present invention encompasses a process for the preparation of Riociguat of Formula I comprising the steps of:

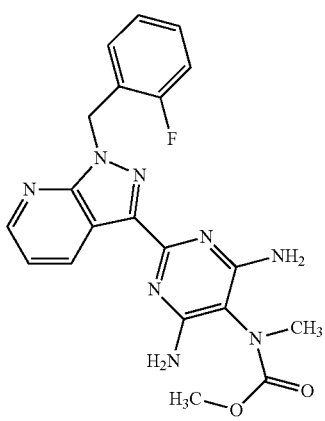

Formula I a) reaction of a compound of Formula I with a suitable acid in a suitable solvent to give a compound of Formula I′ which optionally was isolated,

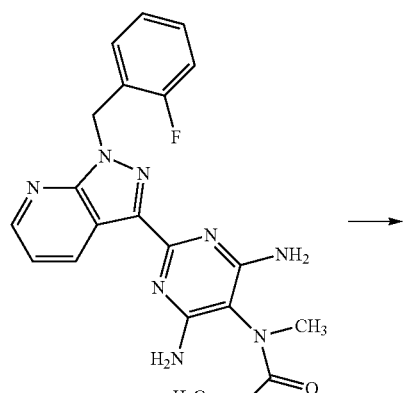

Formula I

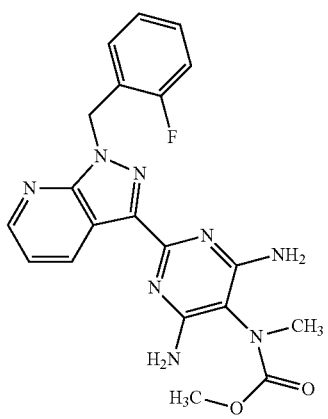

Formula I' b) reaction of the compound of Formula I' with a suitable base in a suitable solvent to give the compound of Formula I.

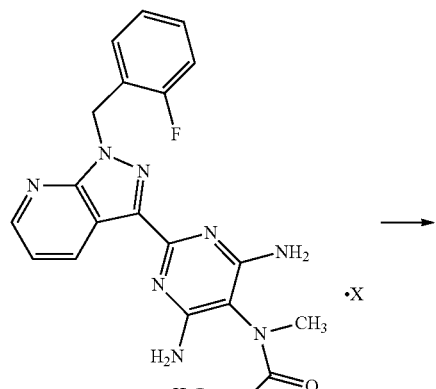

Formula I'

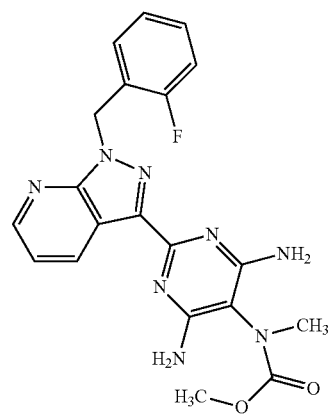

Formula I

In another embodiment, the present invention encompasses process for the preparation of Riociguat of Formula I comprising the steps of:

Formula I

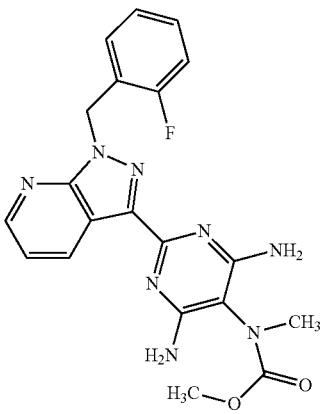

a) reaction of a compound of Formula I with maleic acid and acetonitrile to give a compound of Formula I' which optionally was isolated,

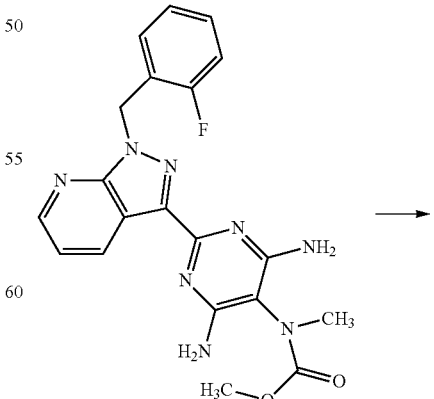

Formula I

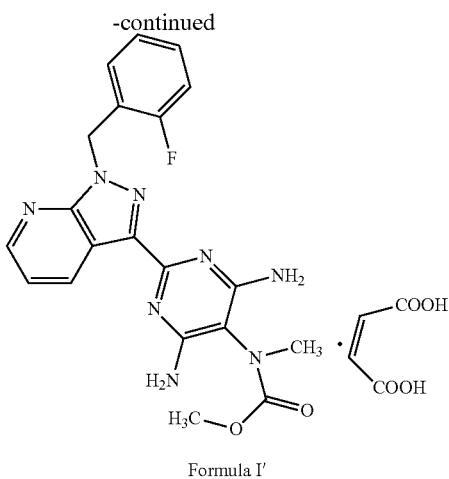

Formula I' b) reaction of the compound of Formula I' with ammonia and methanol to give the compound of Formula I.

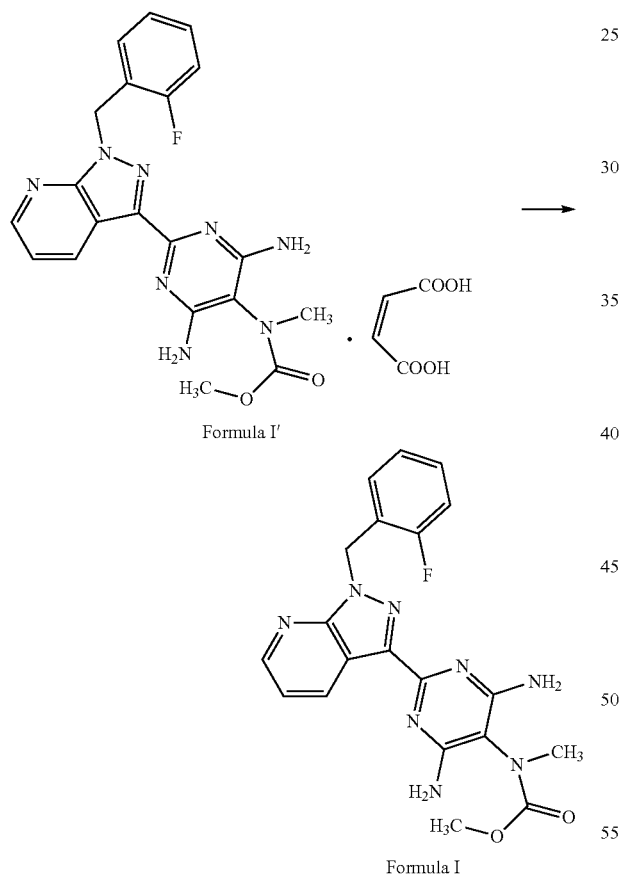

Formula I'

Formula I

In another embodiment, the present invention encompasses use of acid addition salts of Riociguat for the preparation of riociguat.

In another embodiment, the present invention encompasses a crystalline form AL of riociguat.

In another embodiment, the present invention encompasses a process for the preparation of the crystalline form AL of Riociguat comprising reacting an acid addition salt of Riociguat with a suitable base in the presence of water.

In another embodiment, the present invention encompasses a crystalline form AL of Riociguat characterized by an X-ray powder diffraction pattern as shown in FIG. 1.

In another embodiment, the present invention encompasses a crystalline form AL of Riociguat having an X-ray diffraction pattern comprising peaks at 2-theta angles of 11.3, 11.8, 16, 16.56, and 20.28±2Ø.

In another embodiment, the present invention encompasses a hydrated crystalline form AL of riociguat.

In another embodiment, the present invention encompasses a crystalline form AL of Riociguat having a moisture content of about 3.5%, more preferably 2.5%.

In another embodiment, the present invention encompasses Riociguat maleate.

In another embodiment, the present invention encompasses Riociguat oxalate.

Figure 2:
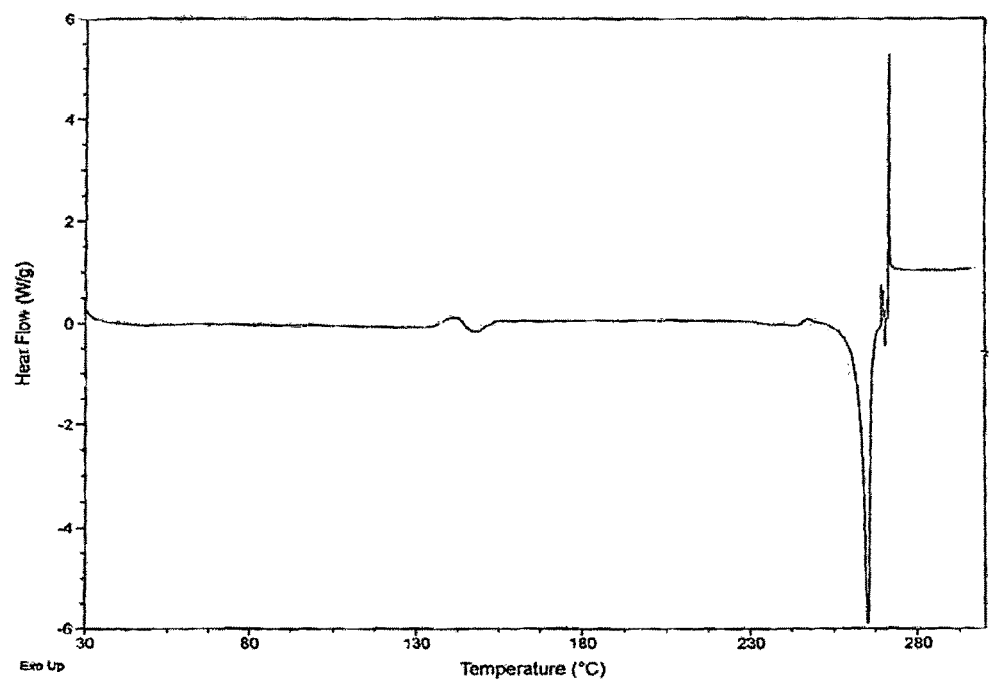
FIG. 2: shows the DSC pattern of form AL of riociguat.

In another embodiment, the present invention encompasses form AL of Riociguat characterized by a DSC pattern as shown in FIG. 2.

Figure 3:
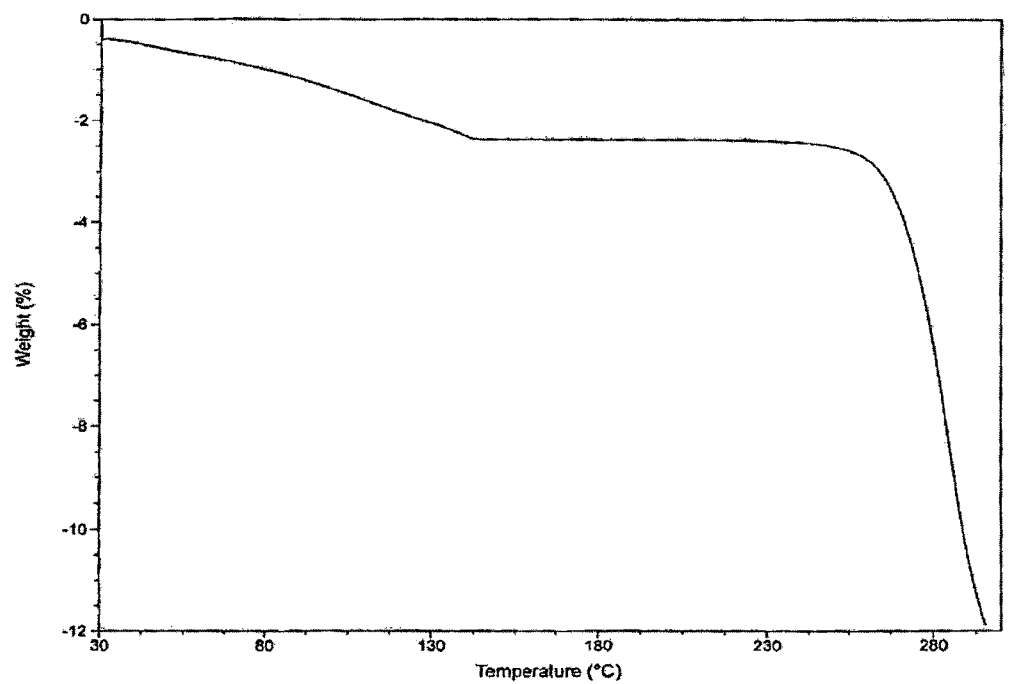
FIG. 3: shows the TGA pattern of form AL of riociguat.
Figure 4:
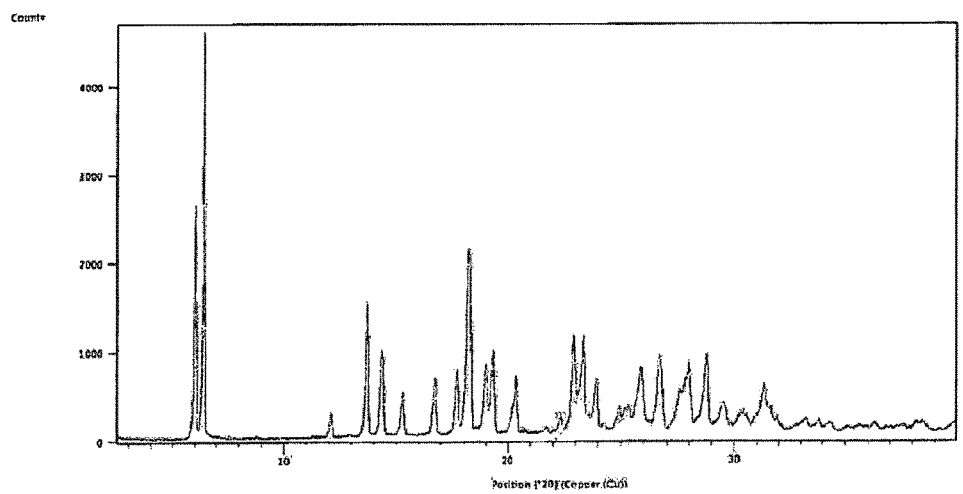
FIG. 4: shows the X-ray powder diffraction pattern of Riociguat maleate.
Figure 5:
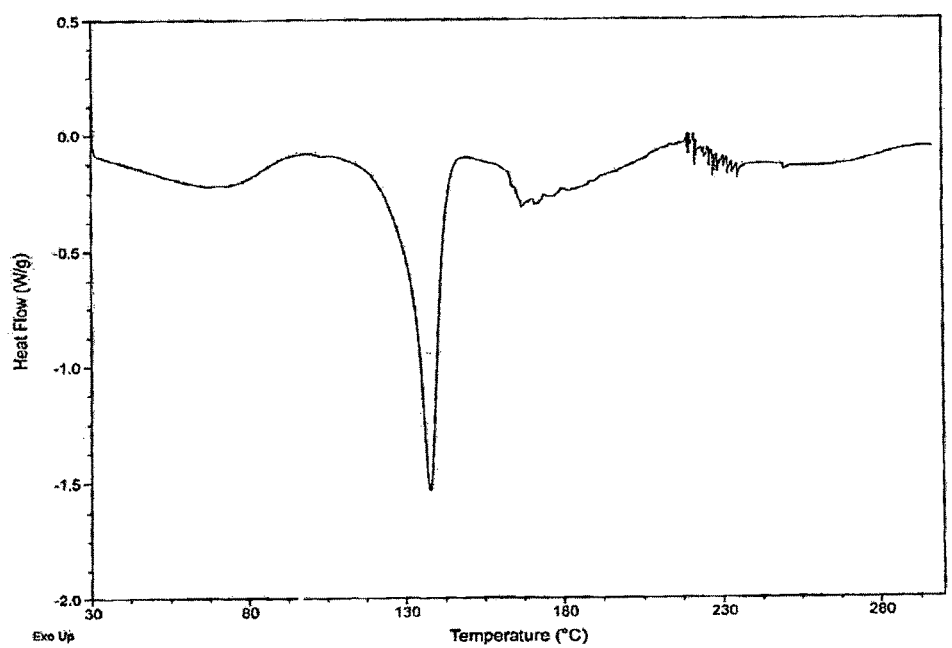
FIG. 5: shows the DSC pattern of Riociguat maleate.
Figure 6:
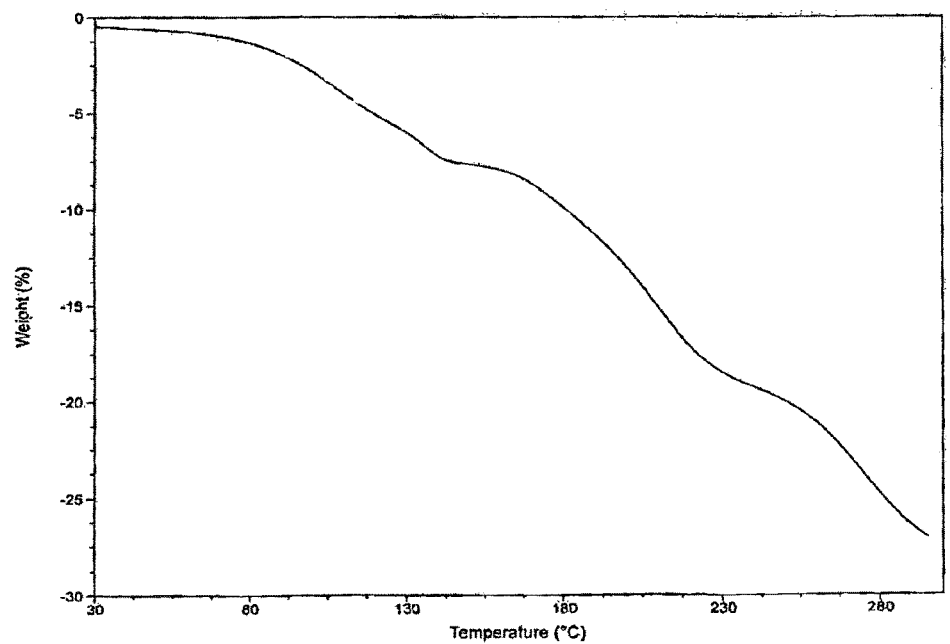
FIG. 6: shows the TGA pattern of Riociguat maleate.

In another embodiment, the present invention encompasses form AL of Riociguat characterized by a TGA pattern as shown in FIG. 3.

In another embodiment, the present invention encompasses the acid addition salts of Riociguat including their hydrates, solvates, anhydrous form and non-solvated form, in crystalline and amorphous forms.

In another embodiment, the present invention encompasses a process for the preparation of acid addition salts of Formula I comprising reacting Riociguat of Formula I with a suitable acid in the presence of a solvent.

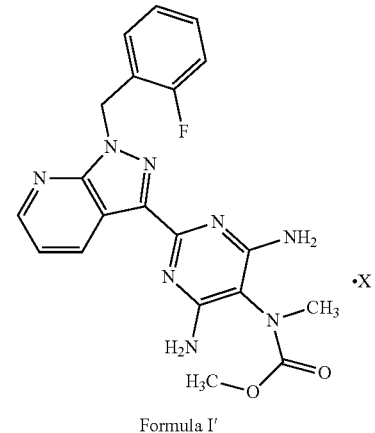

Formula I'

In another embodiment, the present invention encompasses use of acid addition salts of Riociguat for the preparation of a crystalline form AL of riociguat.

In another embodiment, the present invention encompasses a process for the preparation of Riociguat comprising reacting an acid addition salt of Riociguat with a suitable base in the presence of a suitable solvent.

In another embodiment of the present invention encompasses a process for the preparation of Riociguat of Formula I comprising the steps of:

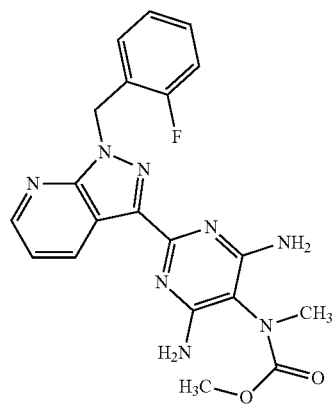

Formula I a) reaction of a compound of Formula II with a compound of Formula III in the presence of suitable base in a suitable solvent to obtain a compound of Formula IV which optionally was isolated,

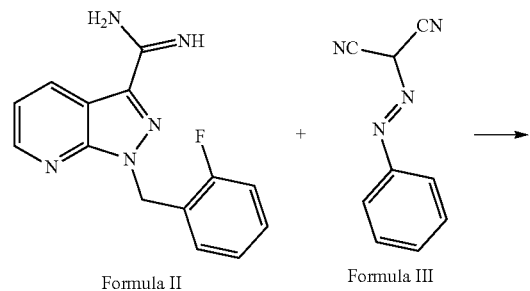

Formula II    Formula III

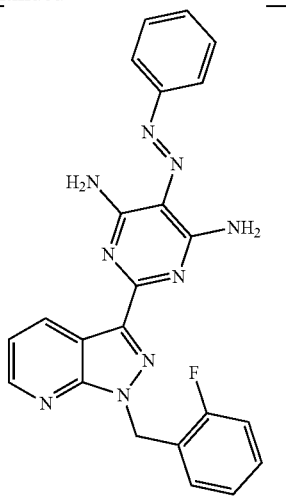

Formula IV b) catalytic hydrogenation of a compound of Formula IV with suitable catalyst in a suitable solvent in the presence of hydrogen to give a compound of Formula V, in situ reacting the compound of Formula V in the presence of methyl chloroformate and suitable base to obtain a compound of Formula VI,

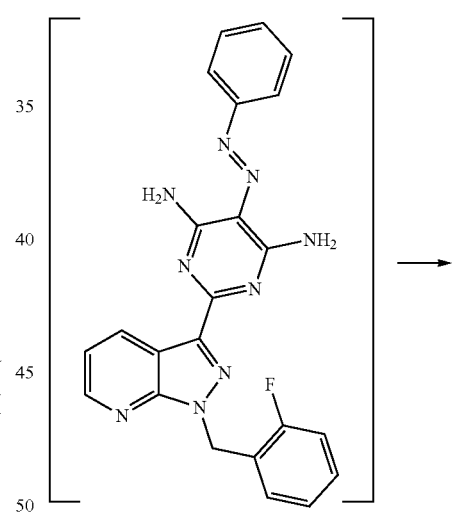

Formula IV

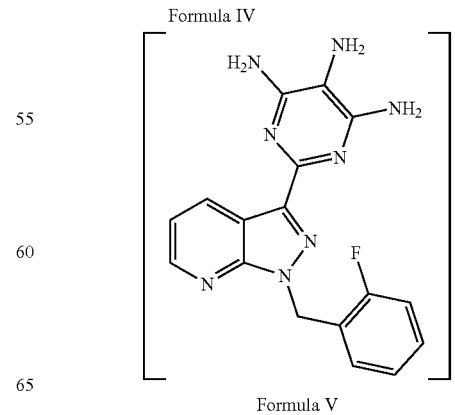

Formula V

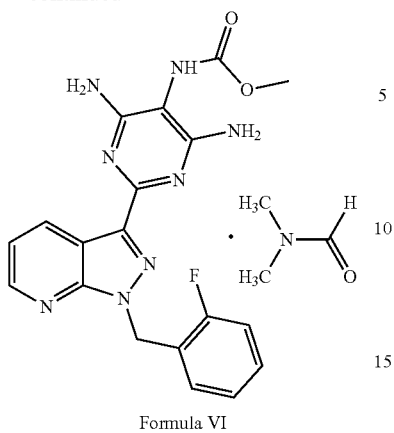

Formula VI c) methylating the compound of Formula VI with a methylating agent in the presence of a suitable base in a suitable solvent to obtain crude Riociguat of Formula I.

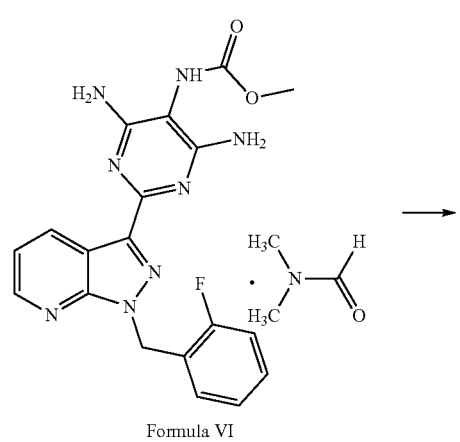

Formula VI

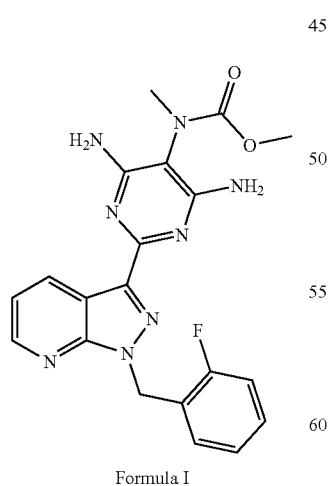

Formula I

In another embodiment of the present invention encompasses a process for the preparation of Riociguat of Formula I comprising the steps of:

Formula I a) reaction of a compound of Formula II with a compound of Formula III in the presence of diisopropyl ethylamine and dimethyl formamide to obtain a compound of Formula IV which optionally was isolated,

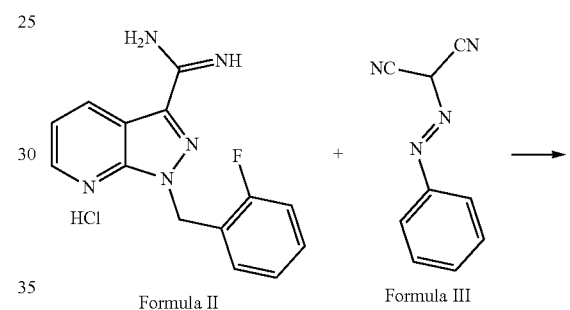

Formula II        Formula III

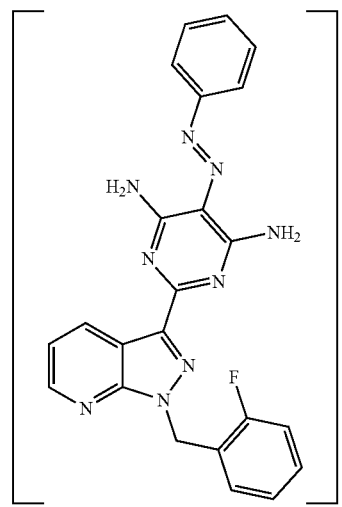

Formula IV b) catalytic hydrogenation of a compound of Formula IV with Raney nickel and dimethylformamide in the presence of hydrogen to give a compound of Formula V, in situ reacting the compound of Formula V in the presence of methyl chloroformate and pyridine to obtain a compound of Formula VI,

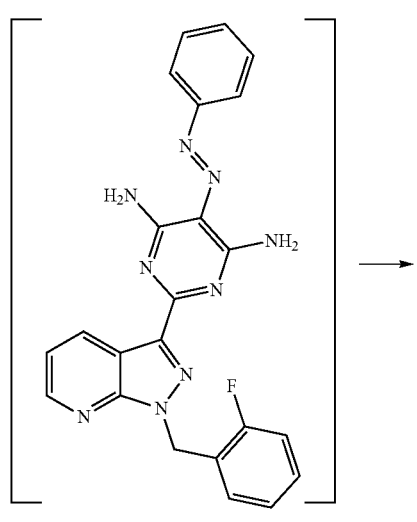

Formula IV

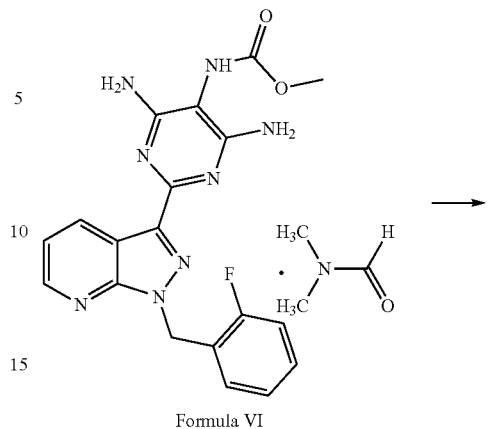

Formula VI

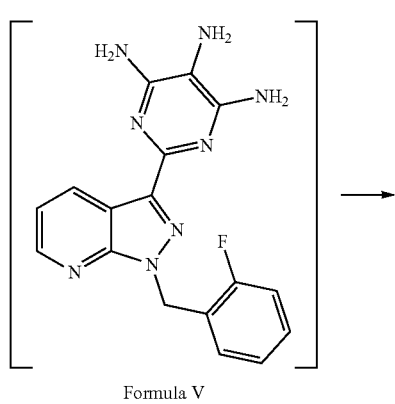

Formula V

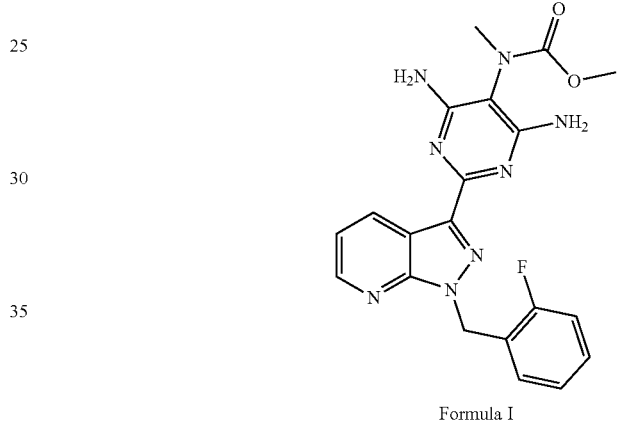

Formula I

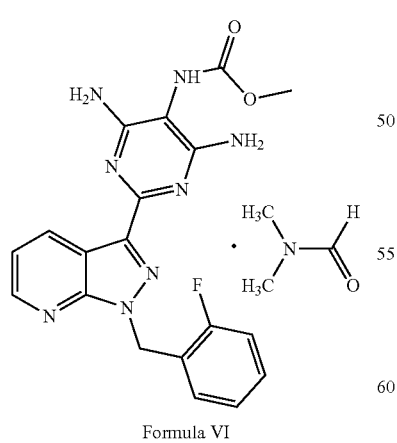

Formula VI c) methylating the compound of Formula VI with methyl iodide in the presence of cesium carbonate and dimethylformamide to obtain crude Riociguat of Formula I.

In another embodiment of the present invention encompasses a process for the preparation of Riociguat of Formula I, comprising the steps of:

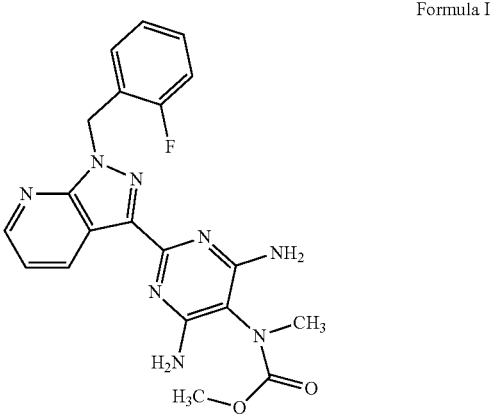 [SMILES: COC(=O)N(C)c1c(N)nc(-c2nn(Cc3ccccc3F)c3ncccc23)nc1N]

Formula I a) reaction of a compound of Formula II with a compound of Formula III in the presence of suitable base in a suitable solvent to obtain a compound of Formula IV which optionally was isolated,

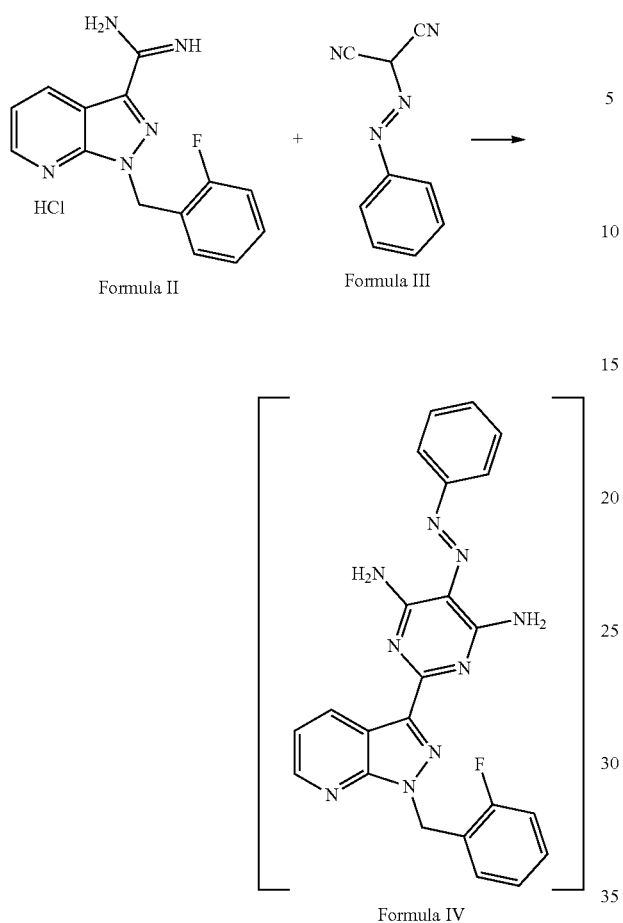

Formula II + Formula III → Formula V

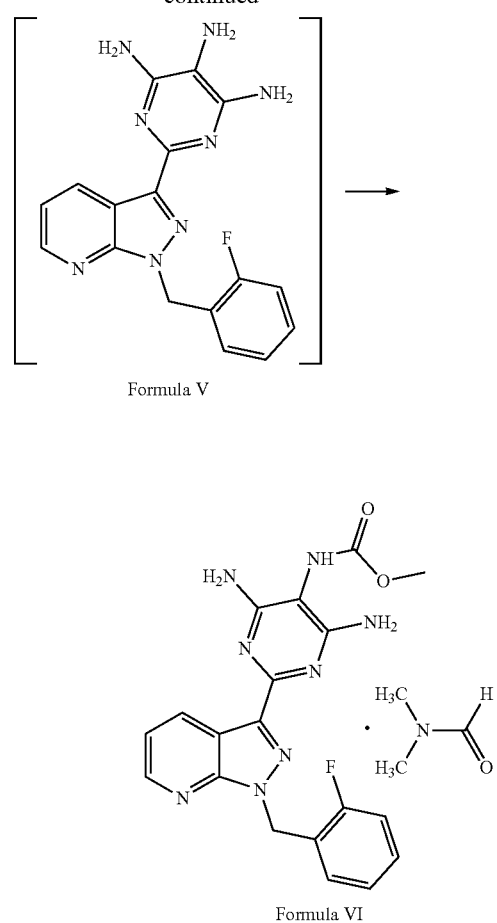

Formula IV b) catalytic hydrogenation of a compound of Formula IV with a suitable catalyst in a suitable solvent in the presence of hydrogen to give a compound of Formula V, in situ reacting the compound of Formula V in the presence of methyl chloroformate, a suitable base in a suitable solvent to obtain a compound of Formula VI, c) N-methylation of the compound of Formula VI with a methylating agent in the presence of a suitable base in a suitable solvent to obtain crude Riociguat of Formula I which optionally was isolated and further treated with a suitable acid in a suitable solvent to obtain the compound of Formula I'.

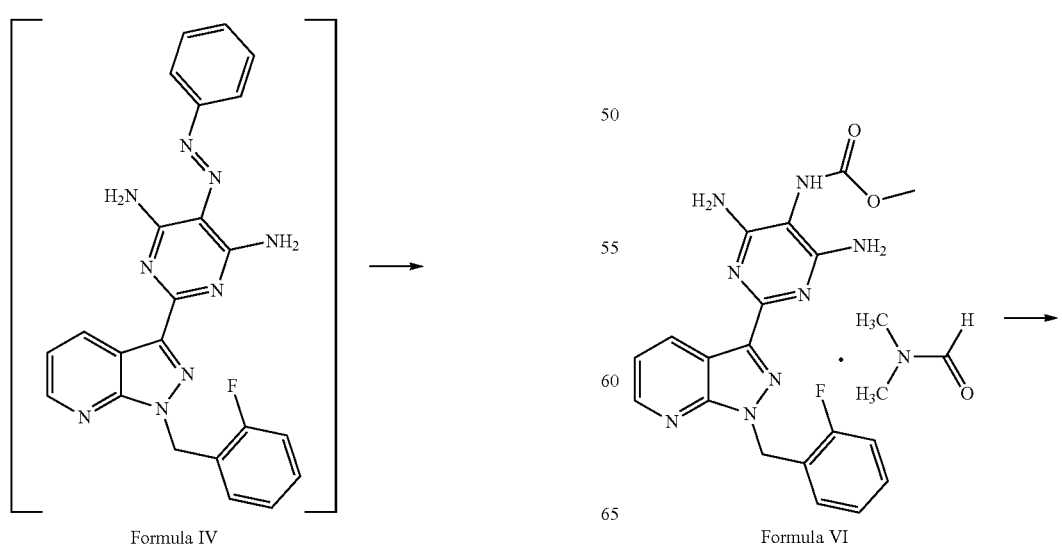

Formula IV → Formula VI →

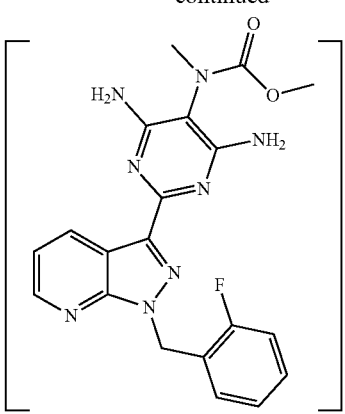

Formula I

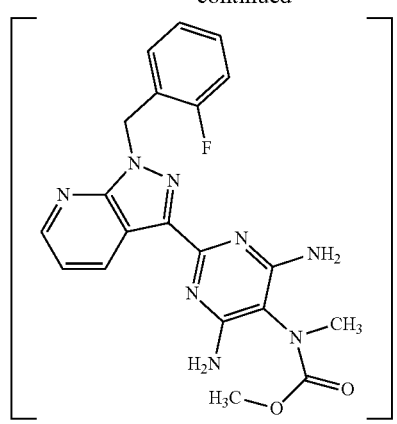

Formula I

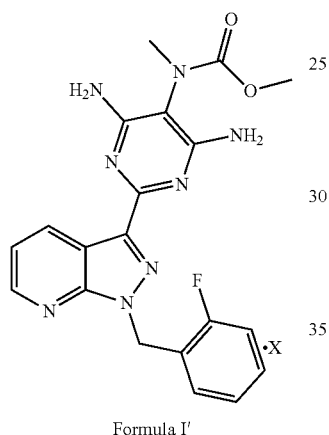

Formula I'

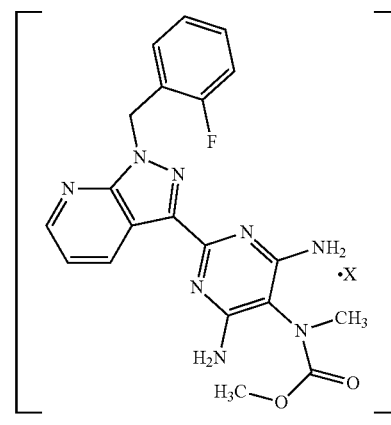

Formula I'' d) treating the compound of Formula I' with a suitable base in a suitable solvent to obtain a compound of formula I which optionally was isolated and further treated with a suitable acid in a suitable solvent to obtain the compound of Formula I'' which optionally was isolated, e) treating the compound of Formula I'' with a suitable base in a suitable solvent to obtain Riociguat of Formula I.

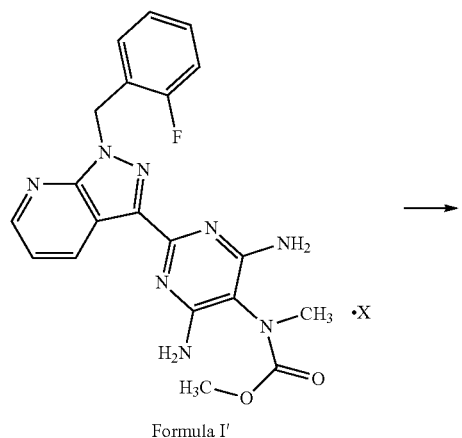

Formula I'

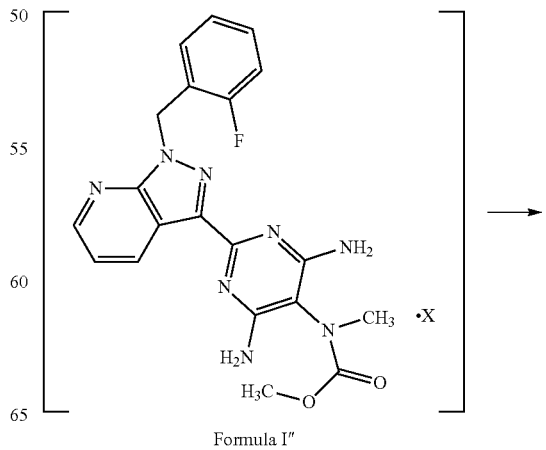

Formula I''

-continued

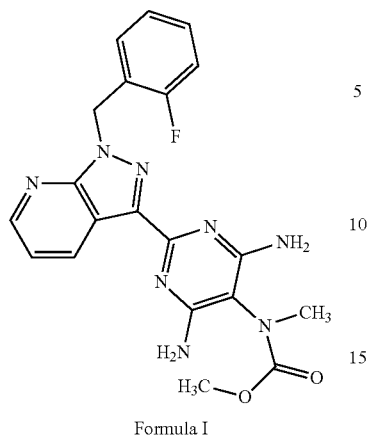

Formula I

In another embodiment, the present invention encompasses a process for the preparation of Riociguat of Formula I, comprising the steps of:

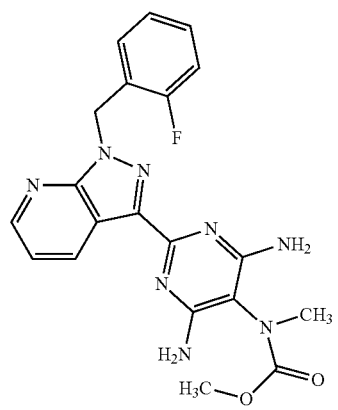

Formula I a) reaction of a compound of Formula II with a compound of Formula III in the presence of DIPEA and DMF to obtain a compound of Formula IV which optionally was isolated,

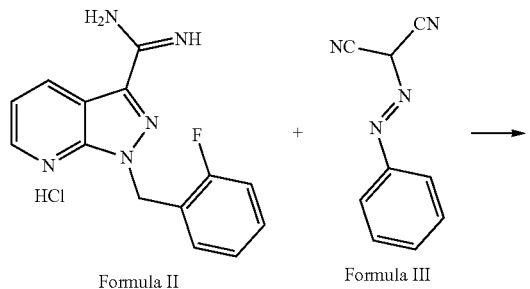

Formula II    Formula III

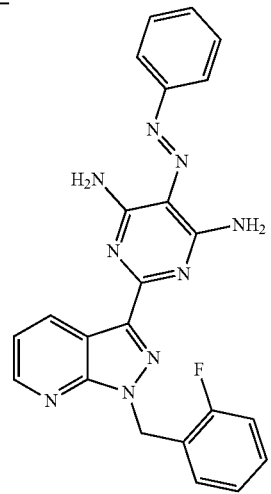

Formula IV b) catalytic hydrogenation of a compound of Formula IV with Raney nickel and DMF in the presence of hydrogen to give a compound of Formula V, in situ reacting the compound of Formula V in the presence of methyl chloroformate pyridine and DMF to obtain a compound of Formula VI,

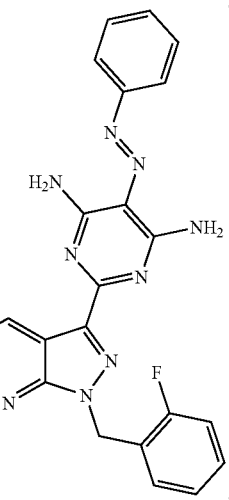

Formula IV

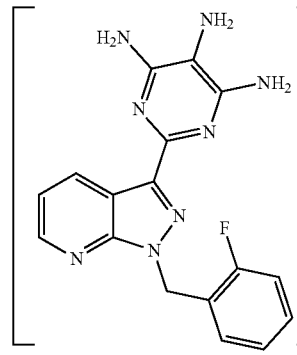

Formula V

37

-continued

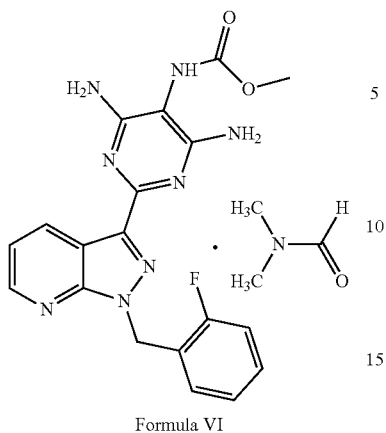

Formula VI c) N-methylation of the compound of Formula VI with methyl iodide in the presence of cesium carbonate and DMF to obtain crude Riociguat of Formula I, which was further treated with maleic acid in acetonitrile and water to obtain the compound of Formula I',

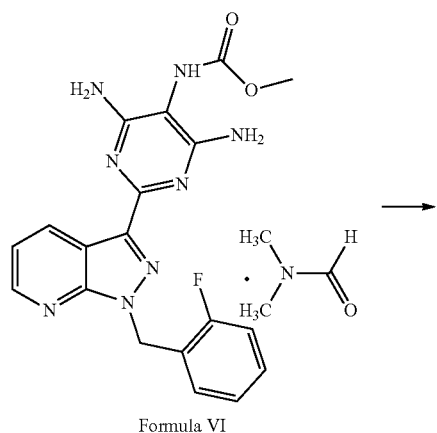

Formula VI

→

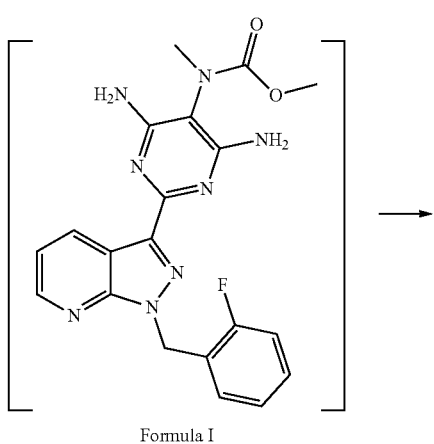

Formula I

38

-continued

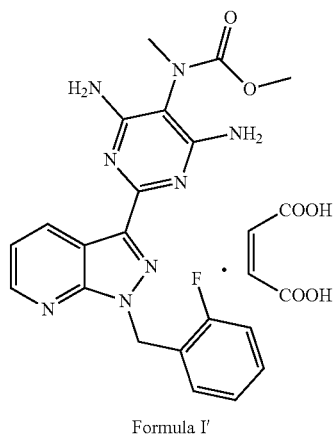

Formula I' d) treating the compound of Formula I' with ammonia and methanol to obtain a compound of formula I which optionally was isolated and further treated with oxalic acid and methanol to obtain the compound of Formula I" which optionally was isolated,

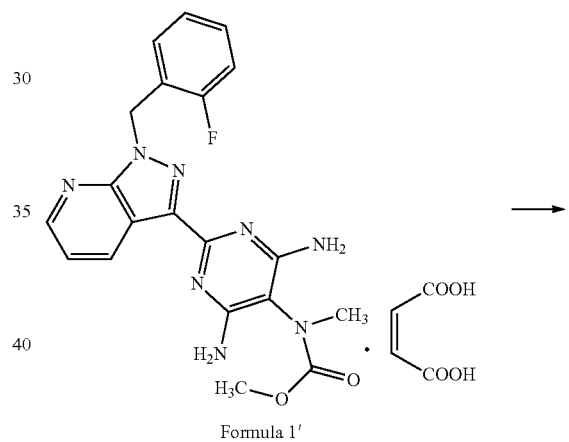

Formula 1'

→

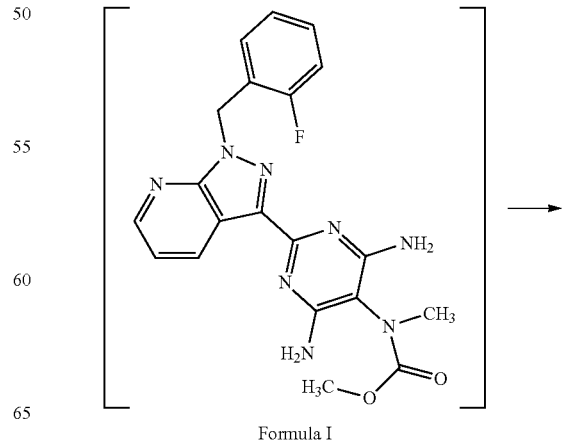

Formula I

-continued

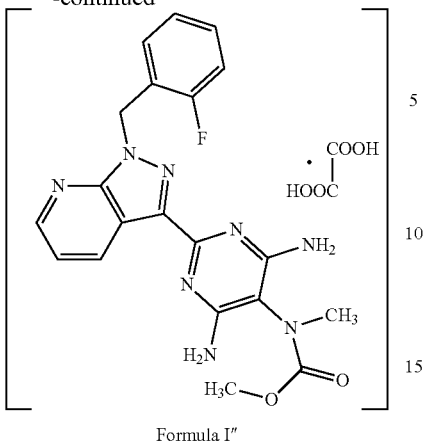

Formula I″ e) treating the compound of Formula I″ with sodium hydroxide and water to obtain Riociguat of Formula I.

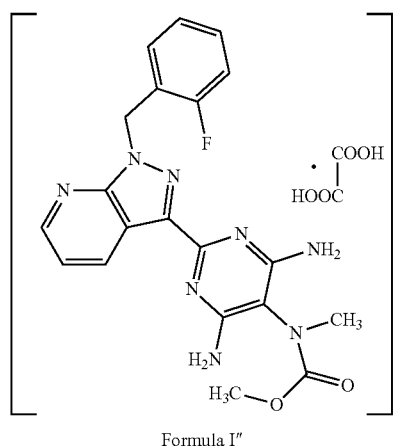

Formula I″

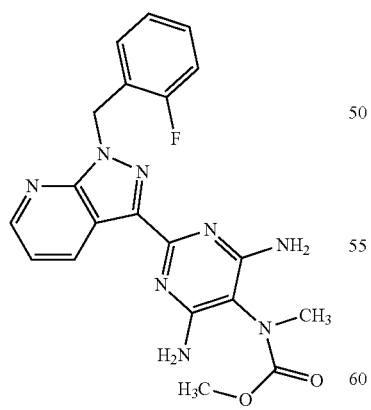

Formula I

In another embodiment, the present invention encompasses a process for the preparation of crystalline form AL of Riociguat of Formula I comprising the steps of:

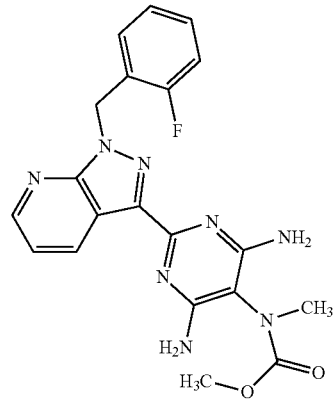

Formula I a) reaction of a compound of Formula II with a compound of Formula III in the presence of DIPEA and DMF to obtain a compound of Formula IV which optionally was isolated,

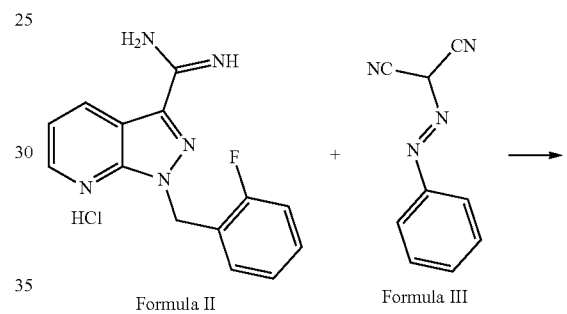

Formula II     Formula III

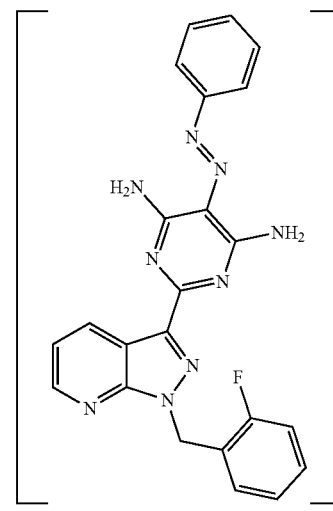

Formula IV b) catalytic hydrogenation of a compound of Formula IV with Raney nickel and DMF in the presence of hydrogen to give a compound of Formula V, in situ reacting the compound of Formula V in the presence of methyl chloroformate pyridine and DMF to obtain a compound of Formula VI,

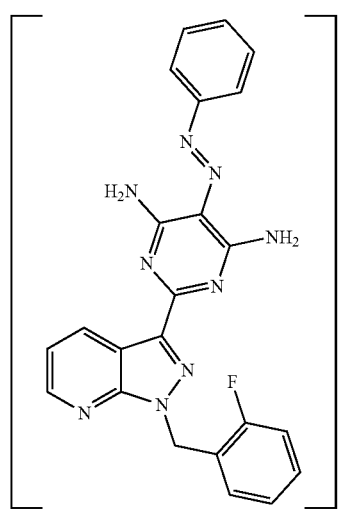

Formula IV

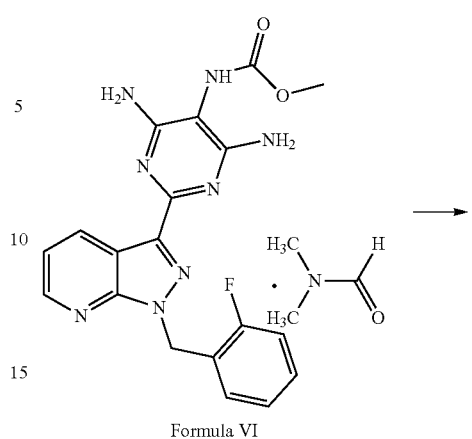

Formula VI

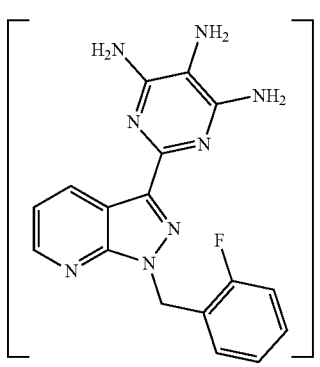

Formula V

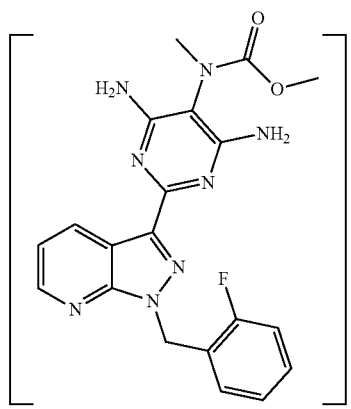

Formula I

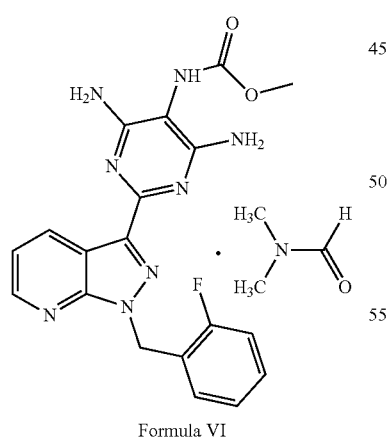

Formula VI

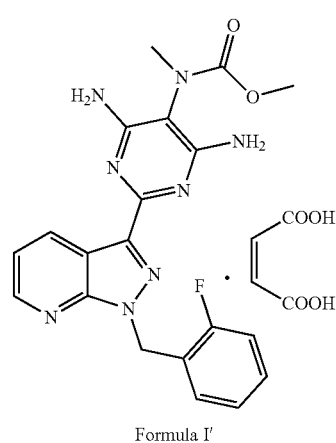

Formula I' c) N-methylation of the compound of Formula VI with methyl iodide in the presence of cesium carbonate and DMF to obtain crude Riociguat of Formula I, which optionally was isolated and further treated with maleic acid in acetonitrile and water to obtain the compound of Formula I'.

d) treating the compound of Formula I' with ammonia and methanol to obtain a compound of formula I, which optionally was isolated and further treated with oxalic acid and methanol to obtain the compound of Formula I" which optionally was isolated,

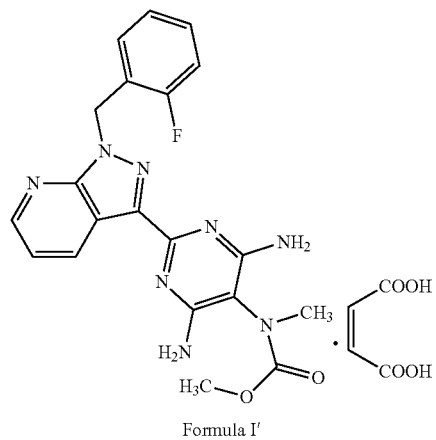

Formula I'

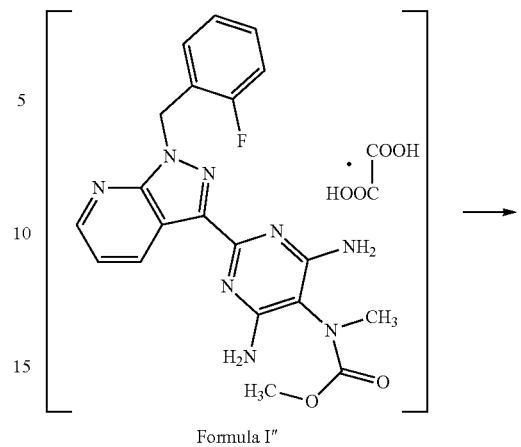

Formula I''

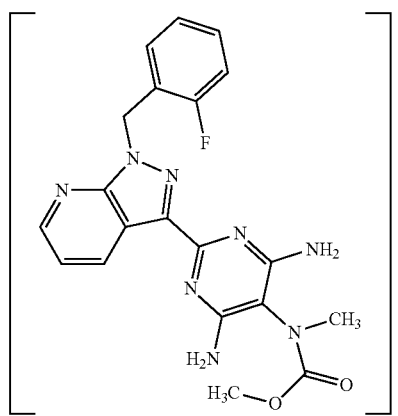

Formula I

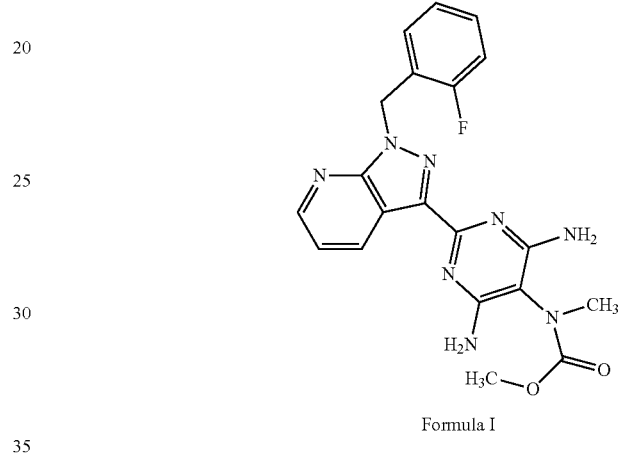

Formula I'' e) treating the compound of Formula I'' with sodium hydroxide and water to obtain a crystalline form AL of Riociguat of Formula I.

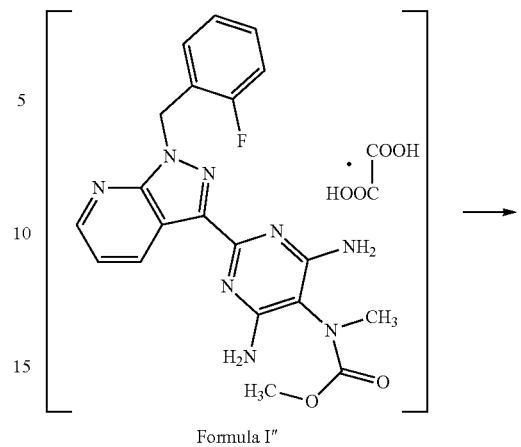

Formula I

The acid addition salts of Riociguat include salts of Riociguat formed with pharmaceutically acceptable inorganic and organic acids. X of the present invention comprises of organic and inorganic acids. Examples of inorganic acids include hydrochloric acid, hydrobromic acid, orthophosphoric acid, and nitric acid.

Examples of organic acids includes acetic acid, 2,2-dichloroacetic acid, adipic acid, ascorbic acid, aspartic acid, benzenesulfonic acid, benzoic acid, 4-acetamido-benzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, salicyclic acid, 4-aminosalicyclic acid, sebacic acid, stearic acid, succinic acid, tartaric acid, thiocyanic acid, toluenesulfonic acid, and undecylenic acid. More preferably, oxalic acid and maleic acid.

The term "solvent" includes any solvent or solvent mixture, for example, water, esters, alcohols, halogenated hydrocarbons, ketones, ethers, polar aprotic solvents, or mixtures thereof.

The suitable solvent of the present invention may be selected from the group consisting of water, alcohols, esters, ketones, ethers, polar aprotic solvents, nitriles or mixtures thereof. Examples of alcohols include those primary, secondary, and tertiary alcohols having from one to six carbon atoms.

Suitable alcohol solvents include methanol, ethanol, n-propanol, 2-propanol, ethylene glycol, PEG and butanol. Examples of ester solvents include ethyl acetate, n-propyl acetate, isopropyl acetate, and n-butyl acetate. Examples of ketones include acetone, methyl ethyl ketone, and the like. Examples of ethers include tetrahydrofuran and the like. A suitable polar aprotic solvent includes N,N-dimethylformamide, N,N-dimethylacetamide, dimethylsulphoxide, acetonitrile, and N-methylpyrrolidone. Examples of halogenated hydrocarbons include dichloromethane, chloroform, and 1,2-dichloroethane. Examples of nitriles such as acetonitrile and the like.

Suitable base of the present invention includes but not limited to an inorganic base or organic base selected from the group comprising of carbonates, bicarbonates, hydroxides, hydrides and alkoxides of alkali or alkaline earth metals and the like, carbonates such as sodium carbonate, potassium carbonate, ammonium carbonate, cesium carbonate, phosphates such as dipotassium monohydrogen phosphate, potassium dihydrogen phosphate, tripotassium phosphate, disodium monohydrogen phosphate, sodium dihydrogen phosphate, trisodium phosphate, diammonium monohydrogen phosphate, ammonium dihydrogen phosphate and triammonium phosphate; acetates such as potassium acetate, sodium acetate and ammonium acetate; formates such as potassium formate and sodium formate; n-butyllithium, n-hexyllithium, sodium hydride and lithium diisopropylamide. These inorganic bases may be used singly, or in combination of two or more kinds thereof. The organic base is selected from the group comprising of lutidine, diisopropylethylamine, dimethylaminopyridine, triethylamine, tri-n-propylamine, tri-n-butylamine, piperidine, pyridine, 2-picoline, 3-picoline, 2,6-lutidine, N-methylmorpholine, N-ethylmorpholine, N,N-diethylaniline, N-ethyl-N-methylaniline, diisopropylethylamine, 3-methylimidazole, 1,8-diazabicyclo[5.4.0]-7-undecene, 1,4-diazabicyclo[2.2.2]octane and 4-dimethylaminopyridine; and metal alcoholates such as sodium methoxide and sodium ethoxide. Other bases are known to the person skilled in the art.

Suitable hydrogenation catalyst is selected from raney nickel, Pt/carbon or Pd/carbon. Preferably hydrogenation catalyst is raney nickel.

Suitable methylating agent is selected from methyl iodide, dimethyl sulphate, methyl toluenesulphonate, etc., and methyl iodide is preferred.

In the foregoing section, embodiments are described by way of an example to illustrate the process of the invention. However, this is not intended in any way to limit the scope of the present invention. Several variants of the example would be evident to persons ordinarily skilled in the art which are within the scope of the present invention.

In the foregoing section, embodiments are described by way of an example to illustrate the process of the invention. However, this is not intended in any way to limit the scope of the present invention. Several variants of the example would be evident to persons ordinarily skilled in the art which are within the scope of the present invention.

EXAMPLES

Example 1: Preparation of 2-[1-(2-Fluorobenzyl)-1H-pyrazolo[3,4-b]pyridine-3-yl]-5-[(E)phenyldiazenyl] 4,6-pyrimidiamine Diisopropylethylamine (64.5 g, 0.5 mol) was added to solution of 1-(2-fluorobenzyl)-1H-pyrazolo [3, 4-b] pyridine-3-carboximidamide hydrochloride (100 g, 0.33 mol) in DMF (300 mL) and phenylazomalanonitrile (68.5 g, 0.4 mol) at room temperature. The resulting reaction mixture was stirred for 8.0 hours at 110-115° C. The progress of reaction was monitored by HPLC. The reaction mixture was cooled to room temperature and stirred for 8.0 hours. The resulting solid material was filtered and washed with cold (0-5° C.) DMF (150 mL) then suck dried to obtain 2-[1-(2-Fluorobenzyl)-1H-pyrazolo [3, 4-b] pyridine-3-yl]-5-[(E) phenyldiazenyl] 4, 6-pyrimidiamine.

Example 2: Preparation of Methyl {4,6-diamino-2-[1-(2-fluorobenzyl)-1H-pyrazolo[3,4-b]pyridin-3-yl] pyrimidin-5-yl}carbamate dimethyl formamide solvate 2-[1-(2-Fluorobenzyl)-1H-pyrazolo [3, 4-b] pyridine-3-yl]-5-[(E) phenyldiazenyl] 4, 6-pyrimidiamine was taken in an autoclave followed by addition of DMF (400 mL) and a slurry of raney nickel (10.0 g) in DMF (100 mL) at room temperature. The resulting autoclaved reaction mixture was flushed with nitrogen gas and hydrogen gas followed by increase the pressure of hydrogen gas up to 6-8 Kg/CM$^2$. The reaction mass was maintained for 6.0 hours at 60-65° C. and the formation of 2-[1-(2-fluorobenzyl)-1H-pyrazolo [3,4-b] pyridin-3-yl]pyrimidine-4,5,6-triamine was monitored by HPLC. The reaction mass was cooled to room temperature and released the hydrogen gas pressure to atmospheric pressure after completion of reaction. Raney nickel catalyst was removed by filtration of reaction mass through hyflo and the hyflo bed was washed with DMF (2×100 mL). The resulting filtrate was charged to next reaction in a round bottom flask (1.0 L) followed by addition of pyridine (14.4 g) at room temperature, then the reaction mixture was cooled to 5-10° C. and methyl chloroformate (54 g, 0.57 mol.) was added. The resulting reaction mixture was stirred for 3.0 hours at 5-10° C. The progress of the reaction was monitored by HPLC. After the completion of reaction, sodium carbonate (86.8 gm) was added with stirring for 2 hours. The obtained precipitate was filtered and washed with DMF (120 ml) and process water (700 ml), dried under vacuum at 55-60° C. to obtain methyl {4,6-diamino-2-[1-(2-fluorobenzyl)-1H-pyrazolo[3,4-b]pyridin-3-yl]pyrimidin-5-yl}carbamate dimethyl formamide solvate. (110 g, 76% yield, >97% HPLC purity).

Example 3: Preparation of Riociguat

Methyl {4,6-diamino-2-[1-(2-fluorobenzyl)-1H-pyrazolo [3,4-b]pyridin-3-yl]pyrimidin-5-yl}carbamate dimethyl formamide solvate (100 g, 0.225 mol) was added to stirring DMF (400 mL) and cesium carbonate (220 g, 0.68 mol) at room temperature. The resulting reaction mixture was stirred for 1.0 hour then a solution of methyl iodide (48 g, 0.34 mol.) in DMF (100 mL) was added. The progress of reaction was monitored by HPLC. After completion of reaction, ENO charcoal (5.0 g) was added and the reaction mass was stirred for 1.0 hour. The reaction mass was filtered through hyflo and hyflo bed was washed with DMF (150 mL). Water (1 L) was added to the above filtrate mass and stirred for 2.0 hours. The obtained precipitate was filtered and washed with water (200 mL) then suck dried to obtain riociguat. (80% yield, >95% HPLC purity).

Example 4: Preparation of Riociguat Maleate

Riociguat was added to stirring acetonitrile (600 ML) and maleic acid (30 g, 0.26 mol) at room temperature. The resulting reaction mixture was stirred for 0.5 hours at room temperature. The reaction mass was heated up to 75-80° C. followed by the addition of water (25-30 mL) at 75-80° C. to obtain a clear solution. The resulting reaction mass was cooled to room temperature and stirred for 4.0 hours. The obtained precipitate was filtered and washed with acetonitrile (100 mL). The wet material was dried under vacuum at 45-50° C. to obtain Riociguat maleate as a pale yellow solid. (115 g, 90% yield, >99% HPLC purity).

Example 5: Preparation of Riociguat

Riociguat Maleate (100 g) was added to stirring Methanol (500 mL) and aqueous ammonia (36 mL) at room temperature. The resulting reaction mixture was stirred for 3.0 hours at room temperature. The obtained precipitate was filtered and washed with Methanol (100 mL). Wet material was died under vacuum at 45-50° C. to obtain riociguat. (75 g, 96% yield and >99% HPLC purity).

Example 6: Preparation of Riociguat Oxalate

Riociguat maleate (100 g) in Methanol (200 ml) was charged in to the round bottomed flask equipped with a mechanical stirrer at 25° C.-35° C. The reaction mixture was stirred 25° C.-35° C. Oxalic acid (28.09 g) in Methanol (200 ml) was added to the reaction mixture at 25-35° C. and was stirred for 2 to 2.5 hours at 25-35° C. The solid formed was collected by filtration and washed with methanol (500 ml) at 25-35° C. The obtained solid was dried in oven under vacuum 45-50° C. to give Riociguat oxalate. (110 g, 90%, purity: >95%).

Example 7: Preparation of Riociguat Oxalate

Riociguat (500 ml) in Methanol (500 ml) was charged in to the round bottomed flask equipped with a mechanical stirrer at 25° C.-35° C. The reaction mixture was stirred 25° C.-35° C. Oxalic acid dihydrate (32.80 g) was added to the reaction mixture at 25-35° C. and was stirred for 2 to 2.5 hours at 25-35° C. The solid formed was collected by filtration and washed with methanol (500 ml) at 25-35° C. The obtained solid was dried in oven under vacuum 45-50° C. to give Riociguat oxalate. (110 g, 90%, purity: >95%).

Example 8: Preparation of Crystalline Form AL of Riociguat

Sodium hydroxide (16.39 g in 164 ml water) was added to a reaction vessel containing Riociguat oxalate (100 g) in water (3 L) at about 25° C. to 35° C. The reaction mixture was heated to about 50° C. to about 55° C. and stirred for 30- to 40 min at 50-55° C. The reaction mixture was cooled to about 25° C. to 30° C. and was stirred for about 3 hours at 25-35° C. The solid formed was collected by filtration and washed with water (100 mL). The obtained solid was dried in oven under vacuum at 45° C. to give Form AL of riociguat. (80.0 g, purity: 99.5%).

We claim:

1. Crystalline form AL of Riociguat, having an X-ray diffraction pattern comprising peaks at 2-theta angles of 11.3, 11.8, 16, 16.56, and 20.28 ±2⊖.

2. Crystalline form AL of Riociguat as claimed in claim 1, characterized by X-ray powder diffraction pattern as shown in FIG. 1.

3. Crystalline form AL of Riociguat as claimed in claim 1, characterized by DSC pattern as shown in FIG. 2.

4. Crystalline form AL of Riociguat as claimed in claim 1, characterized by TGA pattern as shown in FIG. 3.

5. A process for the preparation of Crystalline form AL of Riociguat of formula I comprising the steps of;

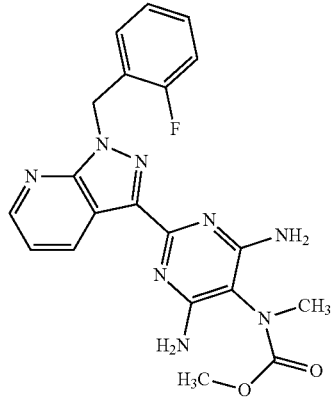

Formula I a) reacting compound of formula I with suitable acid and suitable solvent to give acid addition salts of compound of formula I, and
b) reacting acid addition salts of compound of formula I with suitable base and suitable solvent to give compound Crystalline form AL of Riociguat of Formula I.

6. The process as claimed in claim 5, wherein suitable acids are selected from pharmaceutically acceptable inorganic and organic acids.

7. The process as claimed in claim 6, wherein suitable acids are selected from hydrochloric acid, hydrobromic acid, ortho-phosphoric acid, nitric acid, acetic acid, 2,2-dichloro-acetic acid, adipic acid, ascorbic acid, aspartic acid, benzenesulfonic acid, benzoic acid, 4-acetamido-benzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, salicyclic acid, 4-aminosalicyclic acid, sebacic acid, stearic acid, succinic acid, tartaric acid, thiocyanic acid, toluenesulfonic acid, and undecylenic acid.

8. The process as claimed in claim 5, wherein suitable base is selected from inorganic and organic base.

9. The process as claimed in claim 8, wherein suitable base is selected from sodium hydroxide, potassium hydroxide, ammnonium hydroxide, cesium hydroxide, sodium bicarbonate, potassium bicarbonate, ammnonium bicarbonate, cesium bicarbonate, sodium carbonate, potassium carbonate, ammnonium carbonate, cesium carbonate, sodium hydride, potassium hydride, ammnonium hydride, cesium hydride, dipotassium monohydrogen phosphate, potassium dihydrogen phosphate, tripotassium phosphate, disodium monohydrogen phosphate, sodium dihydrogen phosphate, trisodium phosphate, diammonium monohydrogen phosphate, ammonium dihydrogen phosphate, triammonium phosphate, potassium acetate, sodium acetate, ammonium acetate, potassium formate, sodium formate, n-butyllithium, n-hexyllithium, lithium diisopropylamide, lutidine, diisopropylethylamine, dimethylaminopyridine, triethylamine, tri-n-propylamine, tri-n-butylamine, piperidine, pyridine, 2-picoline, 3-picoline, 2,6-lutidine, N-methylmorpholine, N-ethylmorpholine, N,N-diethylaniline, N-ethyl-N-methylaniline, diisopropylethylamine, 3-methylimidazole, 1,8-diazabicyclo[5.4.0]-7-undecene, 1,4-diazabicyclo[2.2.2]octane and 4-dimethylaminopyridine, sodium methoxide and sodium ethoxide.

10. The process as claimed in claim 5, wherein suitable solvent is selected from water, alcohols, esters, ketones, ethers, polar aprotic solvents or mixtures thereof.

11. The process as claimed in claim 10, wherein suitable solvent is selected from water, methanol, ethanol, n-propanol, 2-propanol, ethylene glycol, PEG, butanol, ethyl acetate, n-propyl acetate, isopropyl acetate, n-butyl acetate, acetone, methyl ethyl ketone, tetrahydrofuran, N,N-dimethylformamide, N,N-dimethylacetamide, dimethylsulphoxide, acetonitrile, N-methylpyrrolidone dichloromethane, chloroform, 1,2-dichloroethane and acetonitrile.

12. The process for the preparation of Crystalline form AL as claimed in claim 1, comprising the steps of; reacting compound of formula I with oxalic acid and methanol to give compound of Formula I″, and

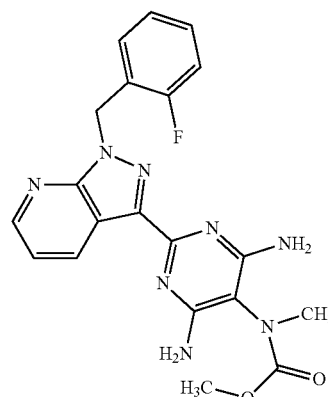

Formula I

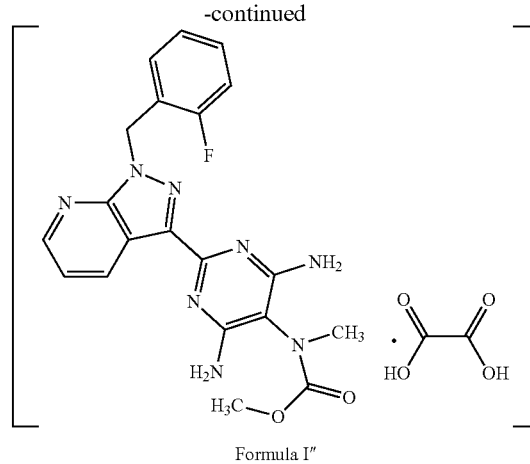

Formula I″ a) reacting compound of Formula I″ with sodium hydroxide and water to give form AL of Riociguat of Formula I

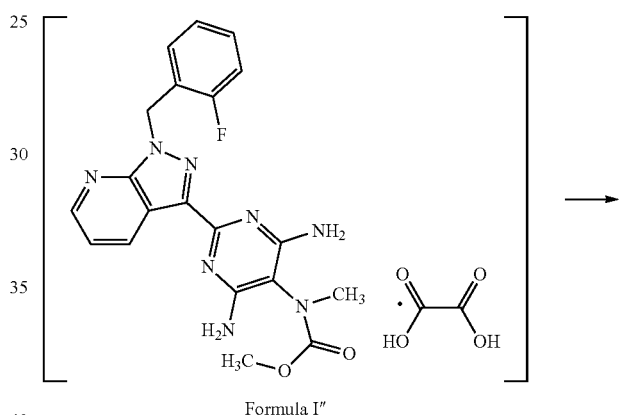

Formula I″

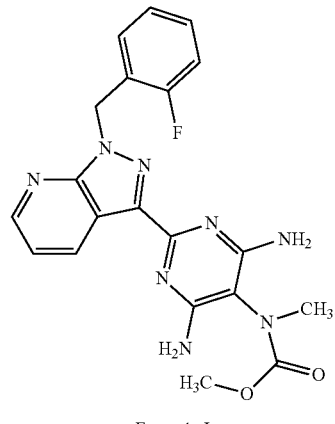

Formula I

* * * * *